(12) United States Patent
Chow et al.

(10) Patent No.: US 10,070,963 B2
(45) Date of Patent: *Sep. 11, 2018

(54) PROSTHETIC FEMORAL STEM FOR USE IN HIGH IMPACT HIP REPLACEMENT

(71) Applicant: Chow IP, LLC, Phoenix, AZ (US)

(72) Inventors: James C. Chow, Paradise Valley, AZ (US); Bjorn N. Rindal, Chandler, AZ (US); Nicholas Slater, Chandler, AZ (US); Joshua A. Butters, Chandler, AZ (US)

(73) Assignee: Chow IP, LLC, Phoenix, AZ (US)

( * ) Notice: Subject to any disclaimer, the term of this patent is extended or adjusted under 35 U.S.C. 154(b) by 99 days.

This patent is subject to a terminal disclaimer.

(21) Appl. No.: 15/221,588

(22) Filed: Jul. 27, 2016

(65) Prior Publication Data
US 2017/0027705 A1    Feb. 2, 2017

Related U.S. Application Data

(60) Continuation of application No. 14/631,486, filed on Feb. 25, 2015, now Pat. No. 9,427,258, which is a
(Continued)

(51) Int. Cl.
*A61F 2/36* (2006.01)
*A61B 17/16* (2006.01)
(Continued)

(52) U.S. Cl.
CPC ........ *A61F 2/3672* (2013.01); *A61B 17/1637* (2013.01); *A61B 17/1668* (2013.01);
(Continued)

(58) Field of Classification Search
CPC ............ A61B 17/1637; A61B 17/1668; A61B 17/175; A61B 17/56; A61B 2017/564;
(Continued)

(56) References Cited

U.S. PATENT DOCUMENTS 2,934,065 A    4/1960    Townley
3,228,393 A    1/1966    Michele
(Continued)

FOREIGN PATENT DOCUMENTS

DE    202005020737 U1    7/2006
EP    0179626 B1    4/1986
(Continued)

OTHER PUBLICATIONS

Oldani, C.R.; Simulation of the Mechanical Behavior of a Hip Implant. Implant Fixed to Bone by Cementation Under Arbitrary Load. Jornal of Physics: 16th Argentine Bioengineering Congress and the 5th Conference of Clinical Engineering. Conference Series 90 (2007) 012007.
(Continued)

*Primary Examiner* — Larry E Waggle, Jr.
(74) *Attorney, Agent, or Firm* — David L. Scott

(57) ABSTRACT

A total hip femoral prosthesis provides a shortened neck and more proximal coating level. Additionally, a means for strengthening the neck may be incorporated to increase stress transfer to the native bone. A method for reducing potential impingement that results from a high neck resection level includes instrumentation for cutting chamfered surfaces into the bone surrounding the proximal end of the implant. Instrumentation and methods of creating chamfered cuts are disclosed.

18 Claims, 30 Drawing Sheets

Related U.S. Application Data division of application No. 13/533,740, filed on Jun. 26, 2012, now Pat. No. 8,992,531, which is a continuation-in-part of application No. 13/366,156, filed on Feb. 3, 2012, now Pat. No. 9,301,765.

(60) Provisional application No. 61/576,792, filed on Dec. 16, 2011.

(51) Int. Cl.
*A61B 17/17* (2006.01)
*A61B 17/56* (2006.01)
*A61F 2/30* (2006.01)

(52) U.S. Cl.
CPC ............ *A61B 17/175* (2013.01); *A61B 17/56* (2013.01); *A61F 2/36* (2013.01); *A61F 2/3601* (2013.01); *A61F 2/367* (2013.01); *A61F 2/3607* (2013.01); *A61F 2/3609* (2013.01); *A61B 2017/564* (2013.01); *A61F 2002/3092* (2013.01); *A61F 2002/3093* (2013.01); *A61F 2002/3611* (2013.01); *A61F 2002/3625* (2013.01)

(58) Field of Classification Search
CPC ........ A61F 2/36; A61F 2/3601; A61F 2/3607; A61F 2/3609; A61F 2002/3611; A61F 2002/3625; A61F 2/3672
See application file for complete search history.

(56) References Cited

U.S. PATENT DOCUMENTS

| | | |
|---|---|---|
| 3,740,769 A | 6/1973 | Haboush |
| 4,038,703 A | 8/1977 | Bokros |
| 4,068,324 A | 1/1978 | Townley et al. |
| 4,279,042 A | 4/1981 | Andriacchi et al. |
| 4,670,015 A | 6/1987 | Freeman |
| 4,738,681 A | 4/1988 | Koeneman et al. |
| 4,895,573 A | 1/1990 | Koeneman et al. |
| 5,035,717 A | 4/1991 | Brooks |
| 5,019,108 A * | 5/1991 | Bertin ................. A61B 17/1659 623/23.28 |
| 5,108,451 A * | 4/1992 | Forte ........................ A61F 2/36 623/22.41 |
| 5,133,766 A | 7/1992 | Halpern |
| 5,169,401 A | 12/1992 | Lester et al. |
| 5,336,226 A | 8/1994 | McDaniel et al. |
| 5,468,243 A | 11/1995 | Halpern |
| 5,593,451 A | 1/1997 | Averill et al. |
| 5,593,452 A | 1/1997 | Higham et al. |
| 5,658,352 A | 8/1997 | Draenert |
| 5,725,594 A | 3/1998 | McTighe et al. |
| 5,755,805 A | 5/1998 | Whiteside |
| 5,776,204 A | 7/1998 | Noble et al. |
| 5,800,560 A | 9/1998 | Draenert |
| 5,951,606 A | 9/1999 | Burke |
| 6,007,581 A | 12/1999 | Noble et al. |
| 6,096,084 A | 8/2000 | Townley |
| 6,102,957 A | 8/2000 | Noble et al. |
| 6,179,877 B1 | 1/2001 | Burke |
| 6,224,605 B1 | 5/2001 | Anderson et al. |
| 6,224,634 B1 | 5/2001 | Keller |
| 6,322,564 B1 | 11/2001 | Surma |
| 6,332,896 B1 | 12/2001 | Hubbard et al. |
| 6,524,343 B2 | 2/2003 | Storer et al. |
| 6,695,884 B1 | 2/2004 | Townley |
| 6,702,854 B1 | 3/2004 | Cheal et al. |
| 6,706,073 B2 | 3/2004 | Draenert et al. |
| 6,723,130 B2 | 4/2004 | Draenert et al. |
| 6,827,741 B2 | 12/2004 | Reeder |
| 6,913,624 B2 | 4/2005 | Hubbard et al. |
| 7,044,975 B2 | 5/2006 | Cheal et al. |
| 7,306,629 B2 | 12/2007 | Saladino et al. |
| 7,323,013 B2 | 1/2008 | McTighe et al. |
| 7,374,576 B1 | 5/2008 | Ries et al. |
| 7,494,509 B1 | 2/2009 | Hershberger et al. |
| 7,527,631 B2 | 5/2009 | Maroney et al. |
| 7,534,271 B2 | 5/2009 | Ries et al. |
| 7,572,297 B2 | 8/2009 | Cheal et al. |
| 7,641,699 B2 | 1/2010 | Unger |
| 7,879,106 B2 | 2/2011 | McMinn |
| 8,075,563 B2 | 12/2011 | Guelat et al. |
| 8,545,506 B2 | 10/2013 | Long et al. |
| 9,301,765 B2 * | 4/2016 | Chow .................... A61B 17/15 |
| 2002/0120344 A1 | 8/2002 | Meulink et al. |
| 2003/0074083 A1 | 4/2003 | LeGros et al. |
| 2003/0078587 A1 | 4/2003 | Lechot et al. |
| 2005/0251145 A1 | 11/2005 | Desarzens et al. |
| 2007/0173847 A1 | 7/2007 | Guelat et al. |
| 2008/0200990 A1 | 8/2008 | McTighe et al. |
| 2009/0281544 A1 | 11/2009 | Anthony et al. |
| 2011/0125155 A1 | 5/2011 | Mutchler et al. |
| 2011/0218537 A1 | 9/2011 | Smith et al. |

FOREIGN PATENT DOCUMENTS

| | | |
|---|---|---|
| EP | 0579868 A3 | 1/1994 |
| EP | 0666069 B1 | 8/1995 |
| EP | 0674886 A1 | 10/1995 |
| EP | 0808618 A2 | 11/1997 |
| EP | 0808618 A3 | 3/1999 |
| EP | 1477120 B1 | 11/2004 |
| FR | 2723530 | 8/1997 |
| WO | WO 97/46179 | 12/1997 |
| WO | WO2009024798 A1 | 2/2009 |

OTHER PUBLICATIONS

Smith, Evert; Neck sparing Stem Designs (Stubbies) Evert Smith 2007-2008 www.evertsmith.com.

Sakai, Rina; Assessments of Different Kinds of Stems by Experiments and FEM Analysis: Appropriate Stress Distribution on a Hip Prosthesis. Clinical Biomechanics Aug. 2005.

Yosibash, Zohar; Subject-Specific p-FE Analysis of the Proximal Femur Utilizing Micromechanics-Based Material Properties. International Journal for Multiscale Computational Engineering, 6(5)483-498(2008).

Smith & Nephew; Synergy Cementless Stem. Surgical Technique, (2004) Nov. 2004 7138-0349.

Taylor, S.J. G.; Telemetry of Forces from Proximal Femoral Replacements and Relevance to Fixation. Journal of Biomechanics vol. 30, No. 3, pp. 225-234 (1997).

Amornsamankul, Somkid; Three-Dimensional Simulation of Femur Bone and Implant in Femoral Canal Using Finite Element Method. International Journal of Mathematics and Computers in Simulation, Issue 4, vol. 4 2010 pp. 171-178.

Toth, Kalman; Early Experience with the DePuy Proxima Short Stem in Total Hip Arthroplasty. Acta Orthop. Belg., 2010,76, 613-618.

Van Ruijven, L.J.; Prediction of Mechanical Properties of the Cancellous Bone of the Mandibular Condyle. Journal of Dental Research (2003) 82: 819.

Bogert, Van Den; An Analysis of Hip Joint Loading during Walking Running, and Skiing. Medicine & Science in sports Exercise, vol. 31(1), Jan. 1999 pp. 131-142.

Which Medical Device, www.whichmedicaldevice.com (Jun. 23, 2011).

Wirtz, Dieter Christian; Critical Evaluation of Known Bone Material Properties to Realize Anisotropic FE-Simulation of the Proximal Femur. Journal of Biomechanics 33 (2000) 1325-1330.

Zimmer; Zimmer M/L Taper Hip Prosthesis. Surgical Techniques, 97-7711-102-00 Rev. 1 2003, 2006, 2010.

Zimmer, Zimmer Mayo Conservative Hip Prosthesis. Surgical Technique, 97-8026-102-00 Rev.2 2002,2003,2006.

Silver, David; Measurement of the Range of Motion in Joints. JBJS 1923 pp. 569-578.

(56) References Cited

OTHER PUBLICATIONS

Chandler, David; Prosthetic Hip Range of Motion and Impingement: The Effects of Head and Neck Geometry. Clinical Orthopaedics 1982 pp. 284.
Freeman, M.A.R.; Why Resect the Neck. JBJS vol. 68B No. 3 May 1986 pp. 346-349.
Noble, Philip C.; The Anatomic Basis of Femoral Component Design. Clinical Orthopaedics and Related Research No. 235, Oct. 1998 pp. 148-165.
Rubin, P.J.; The Morphology of the Proximal Femur. JBJS vol. 74-B, No. 1 Jan. 1992 pp. 28-32.
McTighe, Timothy; New Approch to Neck Sparing Stems. Mini-Symposium AAHKS, Nov. 7, 2008 Dallas, TX.
Falez. F.; Journal of Orthopaedic Trauma. Mar. 2008 9(1); pp. 49-54.
Lombardi, Adolph V.; A Short Stem Solution: Through Small Portal. Orthopedics vol. 32 No. 9 pp. 663 2009.
Bechtol, Charles O.; Neck Sparing Total Hip Arthroplasty—Lessons Learned—AAHKS 2010.
Umer, Masood; Morphology of the Proximal Femur in a Pakistani Population. Jornal of Orthopaedic Surgery 2010;18(3):279-281.
Molfetta, L. Medium Term Follow up of the Biodynamic Neck Sparing Prosthesis. Hip Inter. Jan.-Mar. 2011; 21(1):76-80.
Apex Arc Neck Sparing Hip Replacement. www.omnils.com/products/hip-reconstruction/arc Sep. 8, 2011.
Taperloc Hip System; Biomet Website Sep. 9, 2011; www.biomet.com/orthopedics/productdetail.cfm.
Smith & Nephew; Anthology (Primary Hip System). Surgical Techniques. Jun. 2006 45860101.
Lennox, D.W. Elective Surgery of the Knee. Atlas of Orthopaedic Surgery vol. 3 1991.
Stryker Ortho; Accolade System. Product Brochure, LASB Rev. 3 2010.
Bergmann, G.; Hip Joint Loading During Walking and Running, Measured in two patients. Journal of Biomechanics vol. 26 No. 8 pp. 969-990, 1993.
Biomet; Anterior Supine Intermuscular (ASI) Surgical Technique 2011 Form No. BO10254.1. Rev.013111.
Biomet; Taperloc Complete Hip Joint Replacement Prostheses. Product Insert 01-50-0909 Mar. 2011.
Biomet; Taperloc Hip System. Surgical Technique, 2008 Form No. BO10208.1 Rev.013108.
Public Use Dataset for Normal Joint Range of Motion Data Description and Sample Data Tabels, Oct. 27, 2010.
Public Use Dataset for Normal Joint Range of Motion Methods and Materials Oct. 27, 2010.
Civinini, R. A Ten-Year Follow-up of the Reflection Cementless Acetabular Component, Journal of Bone and Joint Surgery; vol. 90-B, No. 5, May 2008.
Afoke, N.Y.P.; Contact Pressures in the human Hip Joint. The Journal of Bone and Joint Surgery, vol. 69-B, No. 4, Aug. 1987.
Treece, G.M.; High Resolution Cortical Bone Thickness Measurement form clinical CT Data. Med Image Anal. Jun. 2010; 14(3): 276-290.
DePuy; Proxima Hip. Product Summary Jul. 2006.
DePuy; AML Hip System, Surgical Technique. 2002 0612-71-050 (Rev. 1).
Total Hip Prostheses, Self-Centering Hip Prostheses and Hemi-Hip Prostheses Essential Product Information IFU-0902-00-701, Rev. J Created Oct. 24, 2008.
Schmalzried, T.P.; Improving Hip Biomechanics with the Summit Stem. DePuy 2004 0612-61-500 (Rev. 1).
Spitzer, Andrew; Use of the S-ROM Stem in DDH Total Hip Arthroplasty, 2004 0612-74-500.
DePuy; S-ROM Modular Hip System. Surgical Technique 2004 0612-04-503.
Fisher, David; Summit Cementless Stem Early Clinical Results 2005 0612-46-501.
DePuy; Summit Tapered Hip System. Surgical Technique, 2001 0611-80-050 (Rev. 3).
Aesculap Orthopaedics Metha: Implant System(Short Stem) 2008 Doc787.
Patel, Dishita; Infulence of design parameters on cup-stem orientations for impingement free RoM in hip implants. Med. Eng Phys (2011), doi: 10.1016 2011.09.003.
Edwards, Brent W.; Internal Femoral Forces and Moments during running: Implications for stress fracture development. Clinical Biomechanics 23 (2008) 1269-1278.
Exactech; Novation Ceramic AHS Stability in Motion. Jun. 23, 2011.
Fernandez-Valencia, Jenara A.; Short Femoral Stems for Total Hip Arthroplasty. Orhopaedia May 31, 2011.
Zimmer; Fitmore Hip Stem, Product Brochure; 97-0551-001-00 Printed 2008-2009.
Global Ortho; MSA Stem Design Objectives. Jun. 16, 2011.
Wikipedia; Hip Resurfacing Dec. 3, 2011.
Morlock, Michael M. Modes for Implant Failure After Hip Resurfacing: Morphological and Wear Analysis of 267 Retrieval Specimens. JBJS Nov. 14, 2011.
Beck, Thomas J.; Structural Trends in the Aging Femoral Neck and Proximal Shaft: Analysis of the Third National Health and Nutrition Examination Survey Dual-Energy X-Ray Absorptiometry Data. Journal of Bone and Mineral Research vol. 15 No. 12, 2000.
Snyder, Daniel C. The Newest Tissue Sparing Implant Study Group Member. Jan. 2011 pp. 1-9.
Kurtz, William B.; Factors Affecting Bony Impingement in Hip Arthroplasty. The Journal of Arthroplasty vol. 25 No. 4 (2010).
Kurtz, William B. In situ Leg Length Measurement Technique in Hip Arthroplasty. The Jornal of Arthroplasty vol. 00 No. 0 2011.
Tonnis, D.; Normal Values of the Hip Joint for the Evaluation of X-rays in Children and Adults. Reprinted from clinical Orthopaedics, Sep. 1976 vol. 119 pp. 39-47.
OmniLife Science; Apex Arc Neck Sparing Hip Replacements. Jun. 14, 2011 www.omnils.com.
Smith & Nephew; Reflection Interfit Porous-Coated Acetabular Components, Surgical Techniques. 7138-0839 (Jul. 2004).
Semlitsch, M.; Ten Years of Experience with Test Criteria for Fracture-Proof Anchorage Stems of Artificial Hip Joint. MEP Ltd 1983 vol. 12 No. 4.
European Search Report of European App. No. 16178271.9 dated Oct. 26, 2016 (7 sheets).
Australian Examination Report for Australian App. No. 2015201701 dated Mar. 11, 2016 (3 sheets).

\* cited by examiner

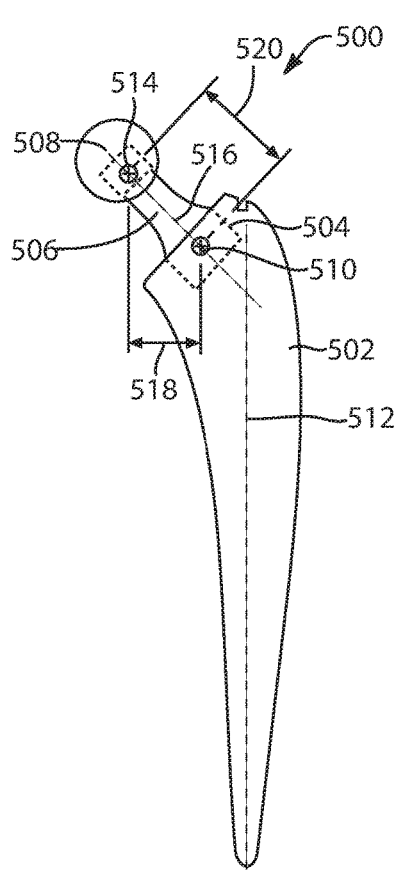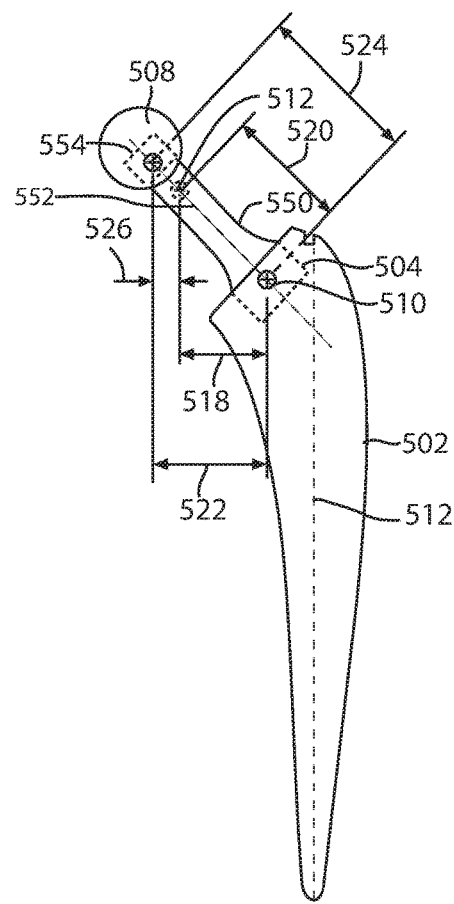
Fig. 5A
(Prior Art)
Fig. 5B
(Prior Art)

| IM Diameter (mm) | Standard Offset (SO) (mm) | High Offset (HO) (mm) | High Impact High Offset (HIHO) (mm) | High Offset Plus (HO⁺) (HO+5mm) |
|---|---|---|---|---|
| 9 | 34 | 40 | 40 | 45 |
| 10 | 35 | 41 | 41 | 46 |
| 11 | 36 | 42 | 42 | 47 |
| 12 | 37 | 43 | 43 | 48 |
| 13 | 37 | 43 | 43 | 48 |
| 14 | 38 | 46 | 46 | 51 |
| 15 | 39 | 47 | 47 | 52 |
| 16 | 40 | 48 | 48 | 53 |
| 17 | 40 | 48 | 48 | 53 |
| 18 | 41 | 49 | 49 | 54 |

PROSTHETIC FEMORAL STEM FOR USE IN HIGH IMPACT HIP REPLACEMENT

CROSS-REFERENCE TO RELATED APPLICATIONS

The present application is a continuation of U.S. patent application Ser. No. 14/631,486, filed Feb. 25, 2015, issued as U.S. Pat. No. 9,427,258, which is a divisional of U.S. patent application Ser. No. 13/533,740, filed Jun. 26, 2012, issued as U.S. Pat. No. 8,992,531, which is a continuation-in-part of U.S. patent application Ser. No. 13/366,156, filed Feb. 3, 2012, issued as U.S. Pat. No. 9,301,765, which claims the benefit of U.S. Provisional Patent Application No. 61/576,792, filed Dec. 16, 2011. The disclosures of each application listed above are incorporated by reference herein in their entireties.

BACKGROUND OF THE INVENTION

This disclosure relates to prostheses and methods for total hip joint replacement. Specifically, this disclosure relates to prostheses that allow for high impact hip joint replacement and to instrumentation and methods for preparing the calcar region of the proximal femur that result in greater bone preservation. A high impact stem design is described that may result in greater bone preservation of the calcar region of the proximal femur, which results in better load sharing and greater overall capability. To ensure that the increase in bone preservation does not result in the limitation of the resulting range of motion, additional instrumentation and techniques are presented that allow the surgeon to create chamfer cuts on the calcar to minimize the potential for impingement.

Total hip replacement procedures seek to replace a hip joint that has deteriorated in its functionality, range of motion, weight bearing and most, if not all, other performance and lifestyle attributes. This degeneration is commonly found in patients that suffer from osteoarthritis, rheumatoid arthritis or osteonecrosis (avascular necrosis). Total hip replacement typically involves amputation of the femoral head, neck and a portion of the top of the femur in order to replace these structures with prosthetic components.

Individual skeletal development and postures vary from person to person. This is in part due to the three dimensional orientation of the hip socket relative to the proximal femur. The distance between the center of rotation of the femoral head and a reliable anatomical landmark, such as the lesser trochanter, may be described as the vertical offset of the head center from the lesser trochanter. This distance may be measured parallel to the femoral shaft axis, and is relevant to postoperative leg length. In the anterior-posterior view (AP view), the distance between the head center and the shaft axis may be described as the lateral offset of the shaft axis from the head center, or as the medial offset of the head center from the shaft axis. It is often referred to simply as "offset." Lateral offset may be relevant to postoperative hip abductor function. Lateral offset is independent of the neck-shaft angle. However, lateral offset may be expressed in terms of the neck-shaft angle and the neck length, which is the distance along the neck axis between the head center and the shaft axis or some other reliable landmark. The neck-shaft angle varies through a range of angles, approximately 127-140 degrees for most people. The neck length varies as well. In the lateral view, the distance between the head center and the shaft axis may be described as the anteversion offset of the head center from the shaft axis, or simply anteversion, if the head center is anteriorly displaced from the shaft axis, or as retroversion if the head center is posterior to the shaft axis. Anteversion or retroversion may be relevant to postoperative range of motion.

Developed by Sir John Charnley in the 1960s, the original Charnley total hip arthoplasty was a stainless steel femoral prosthesis with a small collar, a rectangular cross section and a 22-mm femoral head. Subsequent designs evolved to include different head sizes (22, 25, 25.4 28, 32 and 35 mm), different femoral component lengths (ranging from 110 mm to 160 mm for standard prostheses), different cross sections (square, round, oval, I-beam) and a porous coating for bone ingrowth attachment and metal backing for the acetabulum (cemented or porous coated).

The neck-shaft angle and/or neck length of a prosthesis can also be highly varied in order to replicate natural anatomy or correct deformity. If the neck-shaft angle and/or neck length of a prosthesis are set so that the lateral offset is comparable to an average lateral offset value for intact normal femora, then this prosthesis may be said to have a conventional or standard offset. However, if the neck-shaft angle and/or neck length are set so that the lateral offset is relatively large, this is referred to as a high offset prosthesis. For example, the neck-shaft angle and/or neck length may be set so that the lateral offset is at least 10 mm greater than the average lateral offset value.

Any of the relevant dimensions of a prosthesis may be set so that they are comparable to an average value for intact normal femora. These dimensions may be said to be conventional dimensions. Likewise, any of the relevant dimensions may be set incrementally greater than the corresponding average value, in which case the prosthetic dimensions may be said to be augmented. It follows that smaller than average dimensions may also be selected.

A surgeon will typically measure both hip joints, including the neck-shaft angles, vertical offset, lateral offset, and leg length, prior to performing a total hip replacement procedure. These measurements allow the surgeon to match the replacement joint as closely as possible to the angles and dimensions of the original hip joint in order to achieve satisfactory range of motion, leg length, soft tissue tension, and stability. These measurements may also allow the surgeon to correct deformity or other conditions in and around the operated joint by matching the replacement joint to the contralateral hip joint.

BRIEF DESCRIPTION OF THE DRAWINGS

Various examples of the present technology will now be discussed with reference to the appended drawings. It is appreciated that these drawings depict only typical examples of the invention and are therefore not to be considered limiting of its scope.

FIG. 5A is a front view of yet another prior art total hip femoral prosthesis, with a stem component, a conventional length neck, and a head component; and FIG. 5B is a front view of the stem and head of FIG. 5A with a longer neck component;

DETAILED DESCRIPTION

The present disclosure sets forth a prosthetic high impact femoral hip stem including shortened neck and a means for strengthening the neck. Additionally, the present disclosure sets for a means for reducing potential impingement with the prosthetic hip stem, and maintaining the patient's natural range of motion.

In this specification, standard medical directional terms are employed with the ordinary and customary meanings. Superior means toward the head. Inferior means away from the head. Anterior means toward the front. Posterior means toward the back. Medial means toward the midline, of plane of bilateral symmetry, of the body. Lateral means away from the midline of the body. Proximal means toward the trunk of the body. Distal means away from the trunk. Additionally, standard hip anatomical terms are employed with their ordinary and customary meanings.

Figure 1:
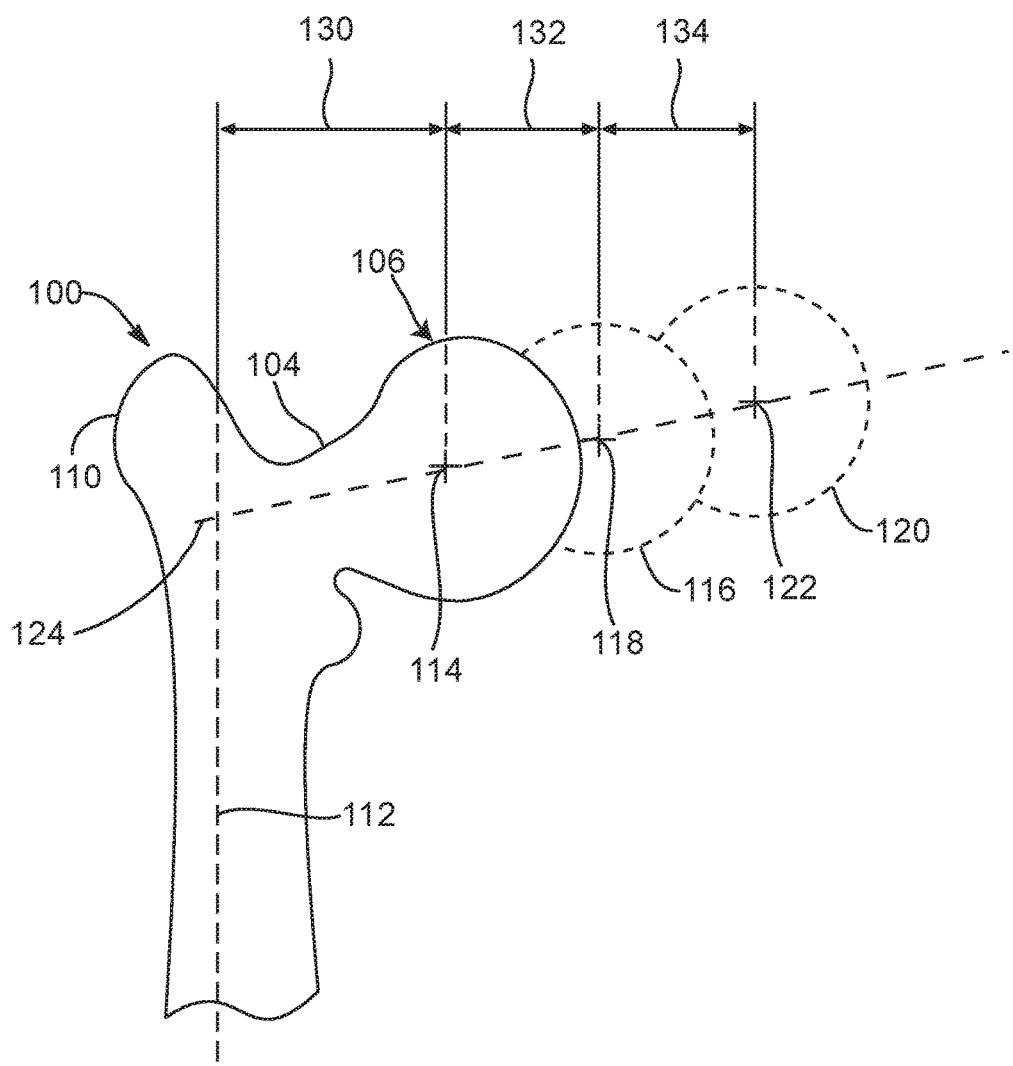
FIG. 1 is a front view of a natural proximal femur, with dashed lines indicating anatomical variants with progressively larger lateral offsets.

Referring to FIG. 1, an intact natural femur 110 is shown in solid lines in a front view, which may also be described as an anterior-posterior (AP) view. The femur 110 has a proximal end 100 which includes a shaft 102, a neck 104 and a head 106. The shaft 102 has a center longitudinal axis 112. The neck 104 has a center longitudinal axis 124 which is oblique to the shaft axis. The head 106 may be approximately spherical. The head has a center point 114, or center of rotation center 114 is spaced apart from the shaft axis 112 by a lateral offset distance 130, which is an average lateral offset value, otherwise known as a conventional offset or standard offset.

Lateral offset 130 may be approximately 39.8 mm to 54.2 mm, based on the work of Rubin, et al. as published in 1992 in the British *Journal of Bone and Joint Surgery* (JBJS BR), volume 74B, pages 28-32, which is incorporated by reference herein in its entirety. Alternately, lateral offset 130 may be 36.2 mm to 49.8 mm, based on the work of Noble, et al. as published in 1988 in *Clinical Orthopedics and Related Research* (CORR), Number 235, pages 148-165, which is incorporated by reference herein in its entirety.

FIG. 1 also illustrates an anatomical variant of femur 110, which has another approximately spherical femoral head 116 with a center point 118. The center 118, which may lie on the neck axis 124, is spaced apart from the shaft axis 112 by a second lateral offset distance 132 which is greater than lateral offset 130. This distance has been exaggerated in FIG. 1 for clarity. This variant may be said to have a high lateral offset. The center 118 may also have a greater vertical offset than center 114 from any reliable anatomical landmark on femur 110, and may thus be offset from the neck axis 124. It can be appreciated that the neck 104 in this variant is naturally long enough to reach from the shaft 102 to the head 116.

FIG. 1 also illustrates another anatomical variant of femur 110, which has yet another approximately spherical femoral head 120 with a center 122. The center 122, which is shown lying on neck axis 124, is spaced apart from the shaft axis 112 by a third lateral offset distance 134 which is greater than the second lateral offset 132. This distance has also been exaggerated in FIG. 1 for clarity. This variant may be said to have a high offset. More specifically, the offset may be characterized as an extra-high offset. The center 122 may also have a greater vertical offset than center 118 from any reliable anatomical landmark on femur 110. It can be appreciated that the neck 104 in this variant is naturally long enough to reach from the shaft 102 to the head 120.

Rubin (JBJS BR 1992) reports offsets up to 62.8 mm. Offsets up to 68.6 mm may be predicted from Rubin's mean of 47.0 mm plus three standard deviations of 7.2 mm. Noble (CORR 1988) reports offsets up to 61.0 mm. Offsets up to 63.4 mm may be predicted from Noble's mean of 43.0 mm plus three standard deviations of 6.8 mm.

Figure 2:
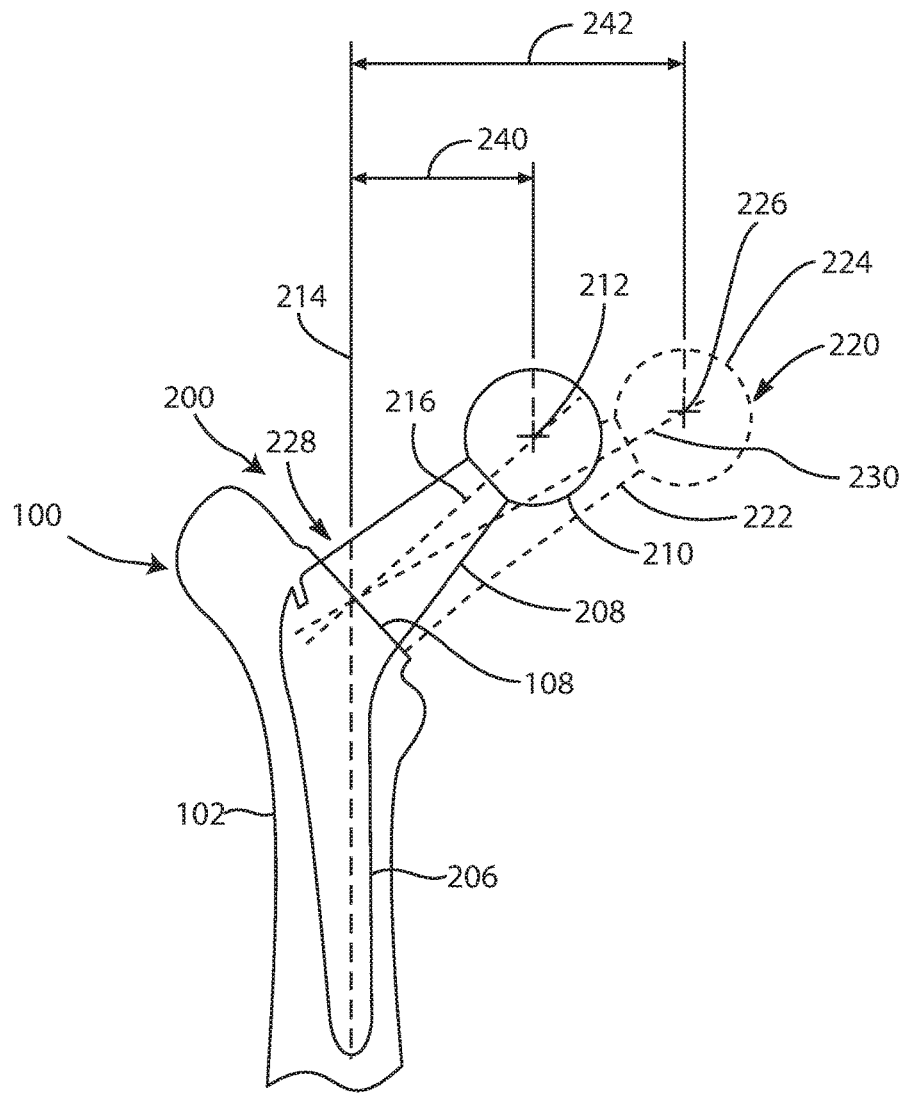
FIG. 2 is a front view of a prior art total hip femoral prosthesis, with dashed lines indicating a variant having a much larger lateral offset and a slightly larger vertical offset.

Referring to FIG. 2, a prior art total hip femoral prosthesis 200 is shown implanted in the proximal end 100 of femur 110. Modular femoral prosthesis 200 includes a stem component 206, a neck component 208, and a head component 210. The neck 208 and head 210 and stem 206 are secured together. The stem 206 is shown within a prepared canal in the femoral shaft 102. A femoral neck osteotomy has been performed, removing the neck 104, head 106, and a portion of the proximal end 100, leaving an angled resection surface 108. The stem 206 has a center longitudinal axis 214 which may align with the shaft axis 112 when the stem is implanted in the shaft 102. The neck 208 has a center longitudinal axis 216 which may be oblique to the stem axis 214. The head 210 is spherical and has a center point 212 which lies on the neck axis 216. The center 212 is spaced apart from the stem axis 214 by a lateral offset distance 240, which is a conventional lateral offset.

FIG. 2 also illustrates another prior art total hip femoral prosthesis 220, which includes the stem 206, another neck component 222, and another head component 224. The neck 222 has a center longitudinal axis 230 which may be oblique to the stem axis 214. The head 224 is spherical and has a center point 226 which lies on the neck axis 230. The center 226 is spaced apart from the stem axis 214 by a lateral offset distance 242 which is greater than lateral offset 240. Lateral offset 242 may be called a high offset compared to lateral offset 240. The center 226 may also have a greater vertical offset than center 212 from any reliable anatomical landmark on femur 110. Neck 222 is approximately 38 mm long measured from base to end along the neck axis 230.

It can be appreciated that high offset neck 222 is longer than conventional neck 208. Therefore, neck 222 may experience higher stresses than neck 208 during use. Neck 222 may bend, crack, or break due to high service stresses and/or accidental overload from trips, slips, falls, or other trauma, particularly over years in vivo. Neck 222 may be expected to fail in or near the indicated region 228. Failure of the neck 222 will require corrective surgery to replace at least the broken neck, with attendant rehabilitation and risks of significant complications.

Figure 3:
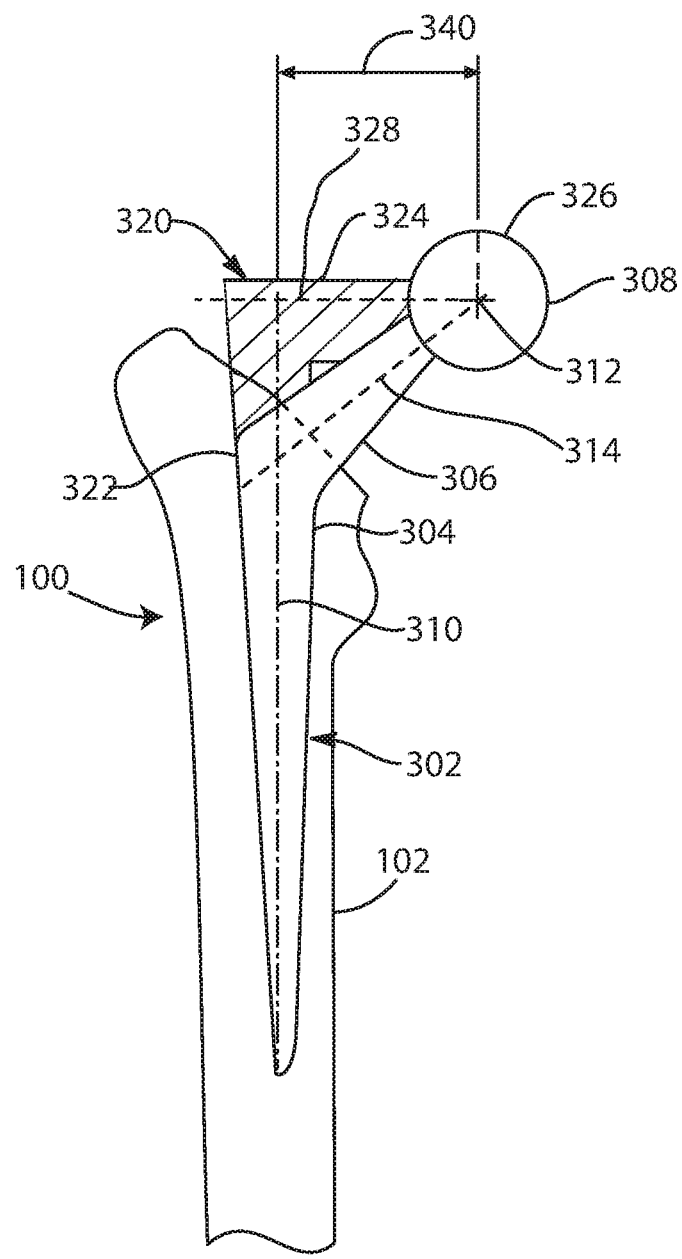
FIG. 3 is a front view of another prior art total hip femoral prosthesis, with a cross-hatched area indicating a variant having a ninety degree neck angle, both prostheses having identical lateral and vertical offsets.

Referring to FIG. 3, a prior art total hip femoral prosthesis 302 is shown implanted in the proximal end 100 of femur 110. Modular femoral prosthesis 302 includes a stem component 304, a neck component 306, and a head component 308. The neck 306 and head 308 and stem 304 are secured together. The stem 304 is shown within a prepared canal in the femoral shaft 102. The femoral shaft 102 has been prepared as set forth above. The stem 304 has a center longitudinal axis 310 which may align with the shaft axis 112 when the stem is implanted in the shaft 102. The neck 306 has a center longitudinal axis 314 which may be oblique to the stem axis 310. The head 308 is spherical and has a center point 312. The center 312 is spaced apart from the stem axis 310 by a lateral offset distance 340.

FIG. 3 also illustrates another prior art total hip femoral prosthesis 320, which includes a longer stem component 322, a horizontal neck component 324 and another head component 326. The stem 322 is aligned with stem axis 310. The neck 324 has a center longitudinal axis 328 which may be perpendicular to the stem axis 310, or nearly so. The head 326 is in the same position as head 308. Therefore, head 326 has the same lateral offset 340 and vertical offset as head 308.

It can be appreciated that neck 324 may be shorter than neck 306, however, stem 322 and neck 324 protrude proximally from femur 110 more than stem 304 and neck 306 do. Therefore, stem 322 and neck 324 may hinder abduction by impinging surrounding anatomical structures, such as the lateral pelvis.

Figure 4:
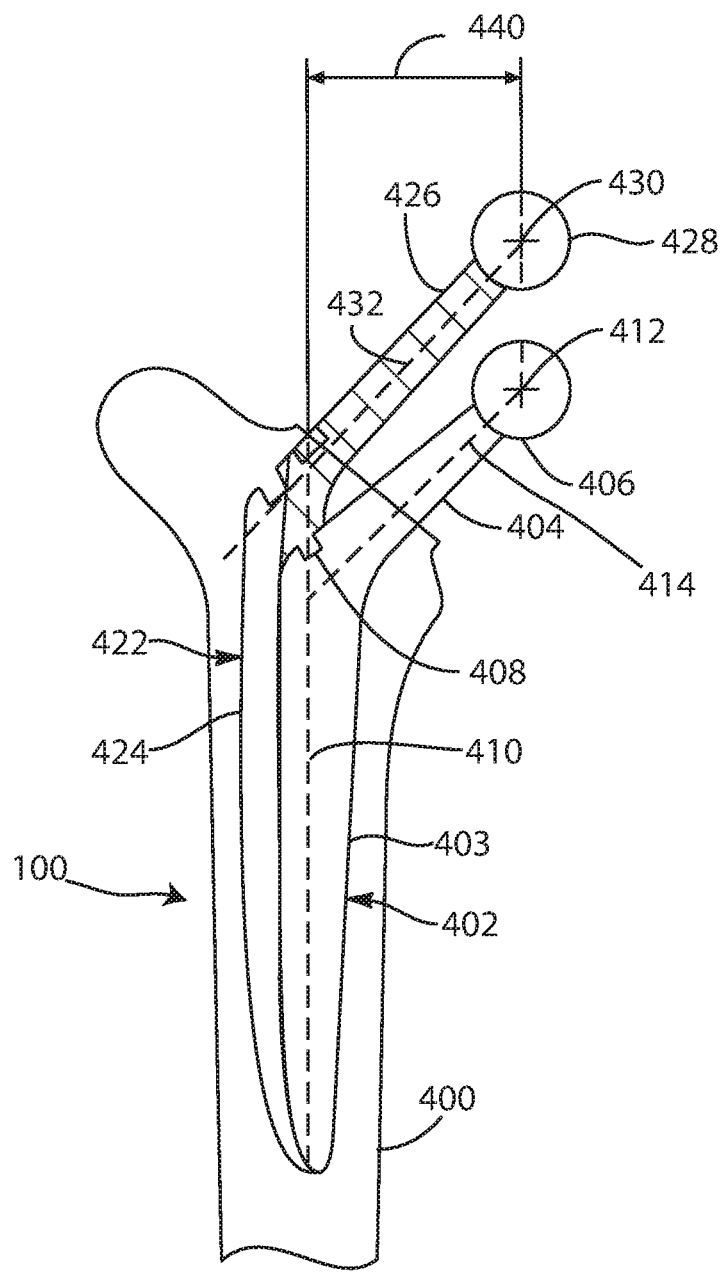
FIG. 4 is a front view of yet another prior art total hip femoral prosthesis, with a cross-hatched area indicating a variant having the same lateral offset and a larger vertical offset.

Referring to FIG. 4, a prior art total hip femoral prosthesis 402 is shown implanted in the proximal end 100 of femur 110. Modular femoral prosthesis 402 includes a stem component 403, a neck component 404, and a head component 406. The neck 404 and head 406 and stem 403 are secured together. The stem 403 is shown within a prepared canal in the femoral shaft 102. The femoral shaft 102 has been prepared as set forth above. The stem 403 has a center longitudinal axis 410 which may align with the shaft axis 112 when the stem is implanted in the shaft 102. The stem 403 has a placement slot 408 for a stem inserter instrument (not shown), a tool used for driving the stem into the prepared canal within the femur. The neck 404 has a center longitudinal axis 414 which may be oblique to the stem axis 410. The head 406 is spherical and has a center point 412. The center 412 is spaced apart from the stem axis 410 by a lateral offset distance 440.

FIG. 4 also illustrates another prior art total hip femoral prosthesis 422, which includes another stem component 424, another neck component 426, and another head component 428. The stem 424 is aligned with stem axis 410. The neck 426 has a center longitudinal axis 432 which may be oblique to the stem axis 410. The head 428 is spherical and has a center point 430. The center 430 is spaced apart from the stem axis 410 by lateral offset distance 440. It can be appreciated that center 430 is farther than center 412 from any landmark on femur 110 in a direction parallel to axis 410. Prosthesis 422 may be said to have a high vertical offset compared to prosthesis 402.

Referring to FIG. 5A, a prior art modular total hip femoral prosthesis 500 includes a stem component 502, a neck component 506, and a head component 508. The neck 506 and head 508 and stem 502 are secured together. The stem 502 has a center longitudinal axis 512 which may align with the shaft axis 112 when the stem is implanted in the shaft 102. The stem 502 also has a pocket 504 which receives a distal portion of the neck 506 when the prosthesis 500 is assembled. The neck 506 has a center longitudinal axis 516 which may be oblique to the stem axis 512. A distal center of rotation 510 may be defined on the neck axis 516 in the distal portion of the neck 506. The distal center of rotation 510 may be in the pocket 504 when the neck 506 is secured to the stem 502. The head 508 is spherical and has a center point 514. The center 514 may coincide with the neck axis 516 in a proximal portion of the neck 506 when the head 508 is secured to the neck 506, thus the center 514 may also be referred to as a proximal center of rotation of the neck. The center 514 is spaced apart from the distal center 510 by a medial-lateral distance 518 and a distance 520 along the neck axis 516. Medial-lateral distance 518 is approximately 20 mm to 50 mm. Distance 520 is approximately 20 mm to 30 mm.

Referring to FIG. 5B, a prior art high offset modular total hip femoral prosthesis includes stem 502 and head 508 with a longer modular neck component 550. The neck 550 has a center longitudinal axis 552 which may be oblique to the stem axis 512. The center of head 508 in this arrangement is at point 554. The center 554 is spaced apart from the distal center 510 by a medial-lateral distance 522 and a distance 524 along the neck axis 552. Distance 524 is greater than distance 520. Medial-lateral distance 522 is greater than medial-lateral distance 518 by the increment 526. Increment 526 is approximately 10 mm to 20 mm. Therefore, medial-lateral distance 522 is approximately 30 mm to 70 mm. Distance 524 is approximately 30 mm to 40 mm. Disadvantageously, the increase in lateral offset places significantly greater stress and strain on the longer modular neck 550, as described for neck 222.

Figure 6A:
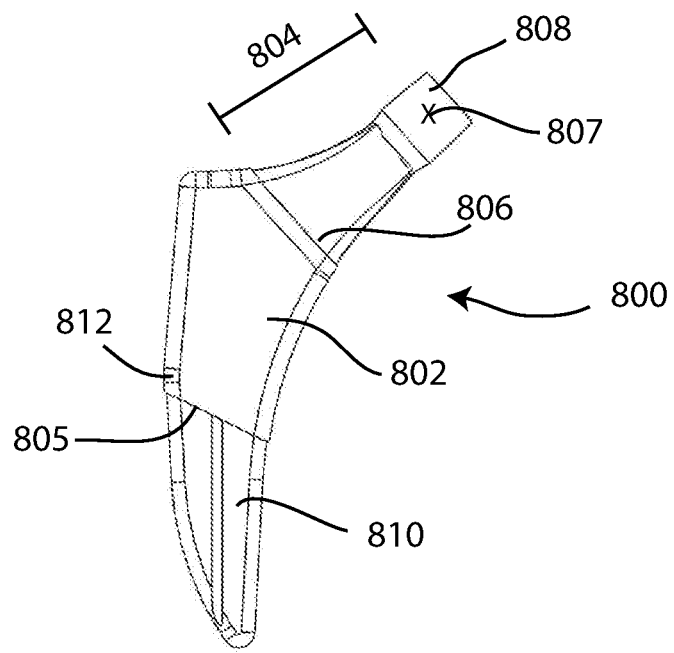
FIG. 6A is a front view of a another prior art total hip femoral prosthesis with a short stem.
Figure 6B:
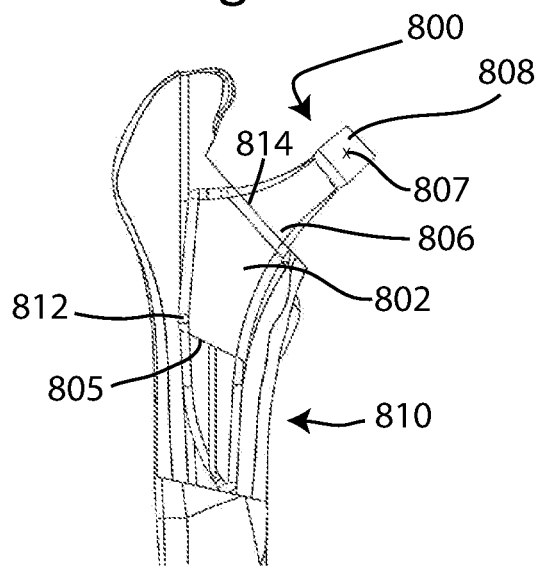
FIG. 6B is a front view of the femoral prosthesis of 6A inserted into a proximal femur with a traditional resection level.

Referring to FIGS. 6A and 6B, a standard, prior art short wedge-style prosthetic hip stem is illustrated with a traditional neck resection level. As illustrated in FIG. 6A, the short wedge-style hip stem 800 includes a traditional porous coating level 802 and a traditional effective neck length 804, as defined by the distance from a proximal boundary 806 of the porous coating level to a center point 807 of a head connection feature 808. The short wedge-style prosthetic hip stem 800 includes a shortened stem portion 810. The shortened stem portion 810 includes an elbow feature 812, which may also be described as a trochanteric relief transition. A distal boundary 805 of the porous coating level is shown below the trochanteric relief transition 812. Referring to FIG. 6B, the standard short wedge-style hip stem 800 is shown inserted into a proximal femur with a traditional neck resection level 814. The neck resection is level corresponds with the proximal boundary 806 of the porous coating.

Having described various commercially available styles of total hip prosthesis, the following description relates to examples of a total hip prosthesis that includes a shortened neck and more proximal coating allowing for a higher neck resection. Another example includes a means for strengthening the neck. Additionally, the following description provides a method for preparing the calcar region such that potential impingement is reduced, allowing the patient to maintain a normal range of motion.

Figure 7:
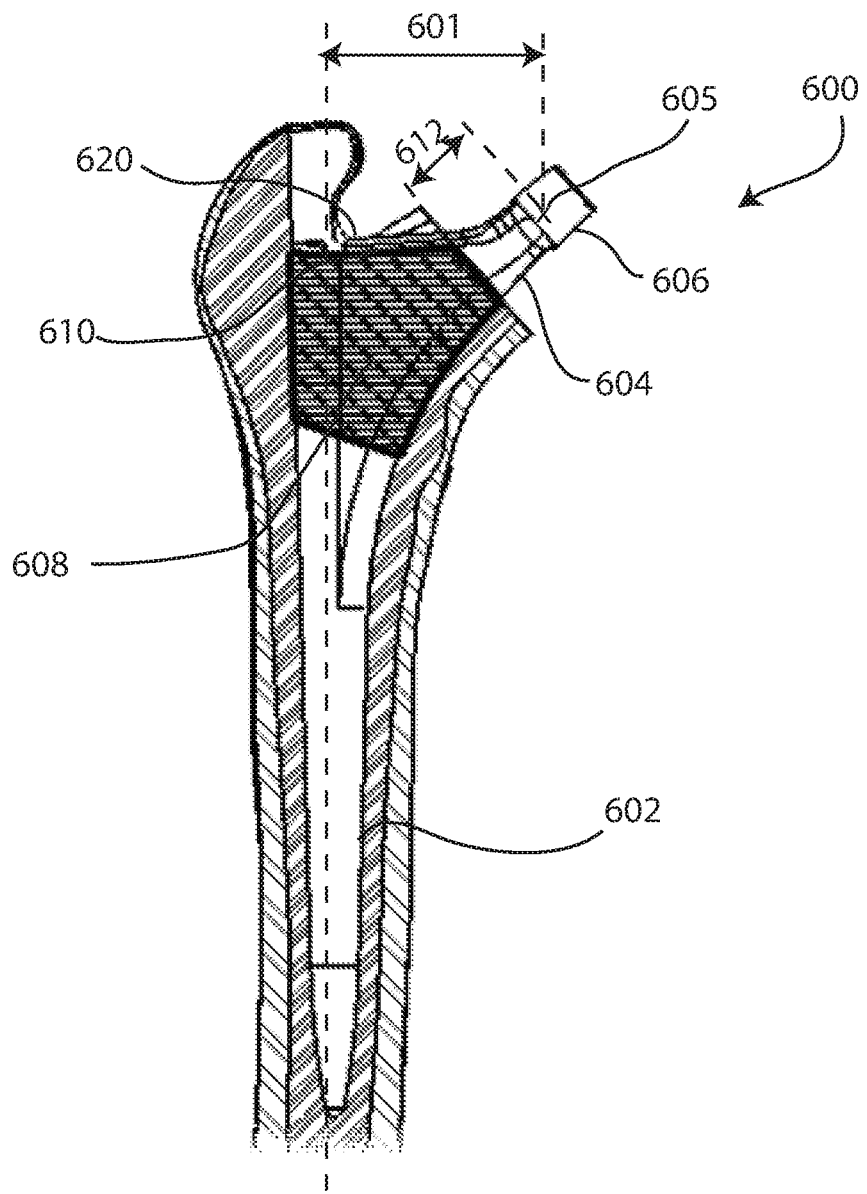
FIG. 7 is a cross section of a prosthetic hip stem with a shortened neck, high resection level inserted and high porous coating level into a femur.

Referring to FIG. 7, an example of a prosthetic femoral hip stem 600 with a shortened neck and more proximal coating is shown implanted into a proximal femur. Femoral hip stem 600 may include features similar to those described in FIGS. 1-6, including a conventional lateral offset 601, a standard stem length and a standard proximal body design. The stem component 602 is shown to extend into the intramedullary canal. Femoral hip stem includes a head connection feature 606 shaped to receive a modular femoral head. Head connection feature 606 may include a center point 605. Additionally, femoral hip stem 600 may be designed for a higher neck resection than is used with conventional stems, allowing for a shortened prosthetic neck 604. The neck 604 may be medialized in this example. The neck axis has been shifted away from the stem axis, compared to a conventional stem. Portions of the stem 602, neck 604 and head connection feature 606 may be fabricated from different materials according to the requirements of each portion.

Femoral hip stem 600 may also include a superior surface 620 that extends along a transverse plane that is proximal to the stem 602, and may intersect a lateral portion of stem 602 and neck 604. In other words, superior surface 620 may blend the superior portions of the stem 602 and a base portion of the neck 604 together. The superior surface may by smooth and planar, or may include surface texture elements such as roughening, and may also be contoured.

The shortened neck 604 may be fabricated with a substrate of one material, and include an exterior coating 608 of another material. The coating 608 may be porous to enhance bone ingrowth around the neck 604. The shortened neck 604 may allow for a high level of porous coating 608, wherein at least a portion of a proximal boundary 610 of the more proximal coating 608 may extend from a proximal portion of the stem 602 along a plane parallel to the superior surface 620. Bone ingrowth onto the shortened neck may facilitate load sharing with the shortened neck, allowing for a high impact application. The proximal boundary 610 of the more proximal coating 608 may then extend distally at an angle across a base portion of the neck 604. The angled portion of the proximal boundary 610 may be located at a first distance 612 from the center point 605 of the head connecting feature 606.

The lateral extent of shortened neck 604 may be defined as the lateral distance between the resection level on the stem, or the porous coating level on the stem, and the center of the head connecting feature 606, or the center of an actual head, if present. More specifically, the lateral extent may be defined as the lateral distance between the intersection of the neck axis and the resection or porous coating level, and the center of the head connecting feature 606, or head. The lateral extent of the shortened neck 604 may be a percentage of the total lateral offset distance described previously, for example with reference to FIG. 1. The lateral extent may be about 50% of the lateral offset, or it may be smaller, such as 40%, 30% or 20% of the total medial offset. For example, if the total lateral offset is 45 mm, the lateral extent may be defined as 30% of the total lateral offset, or 15 mm. It can be appreciated that a smaller lateral extent correlates with a shorter neck, as measured along the neck axis.

Figure 8:
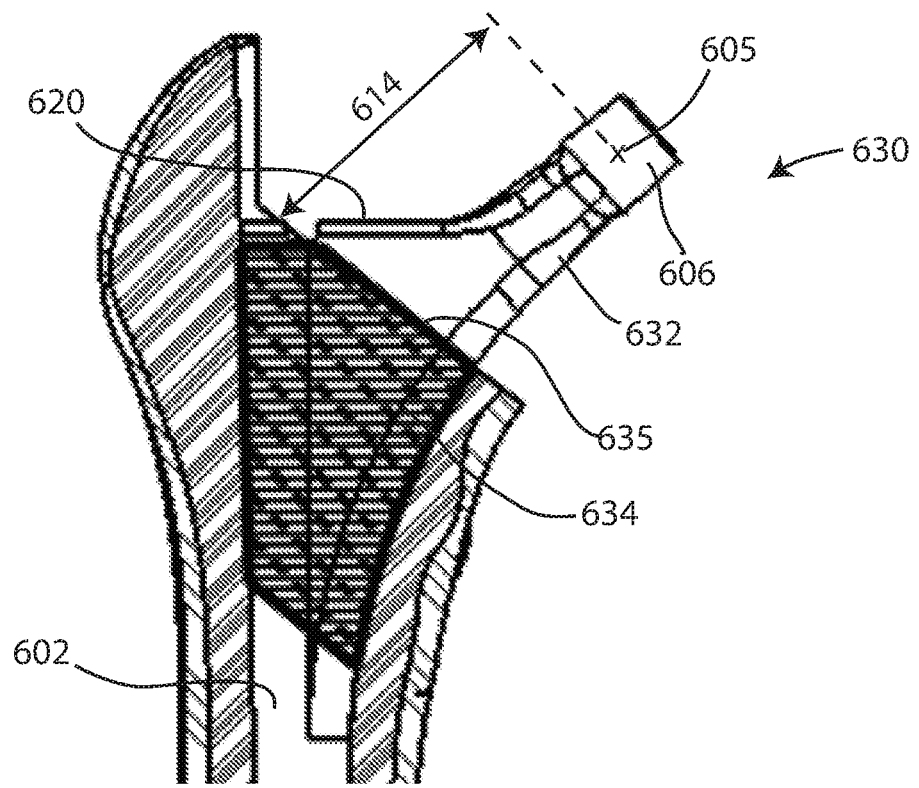
FIG. 8 is a cross section of a proximal femur with inserted hip stem with a traditional porous coating level.

Comparatively, a femoral hip stem that is similar to hip stem 600, but with a longer neck and a traditional porous coating level is shown in FIG. 8. The traditional porous coating has a proximal boundary is located a second distance 614 from the center point 605 of head connecting feature 606, wherein the second distance 614 is larger than the first distance 612 shown in FIG. 6.

By shortening the neck 604 and including a more proximal coating 608, as shown in FIG. 7, the amount of unsupported neck length may be reduced and the moment arm length may be decreased, as a more proximal coating may enhance bony ingrowth closer to the head portion 606, thus reducing the stress put on the neck 606 by increasing the amount of load that can be shared with native bone. The high impact hip stem described in FIGS. 7 and 9-11 is optimized for larger diameter heads (such as ≥36 mm), providing a range of motion comparable to the natural hip joint. By designing the prosthetic neck geometry around a larger diameter prosthetic head, the prosthetic neck length can be shortened while maintaining a desirable ratio between the diameter of the prosthetic head and the diameter of the neck at the level where acetabular impingement would occur.

Figure 9:
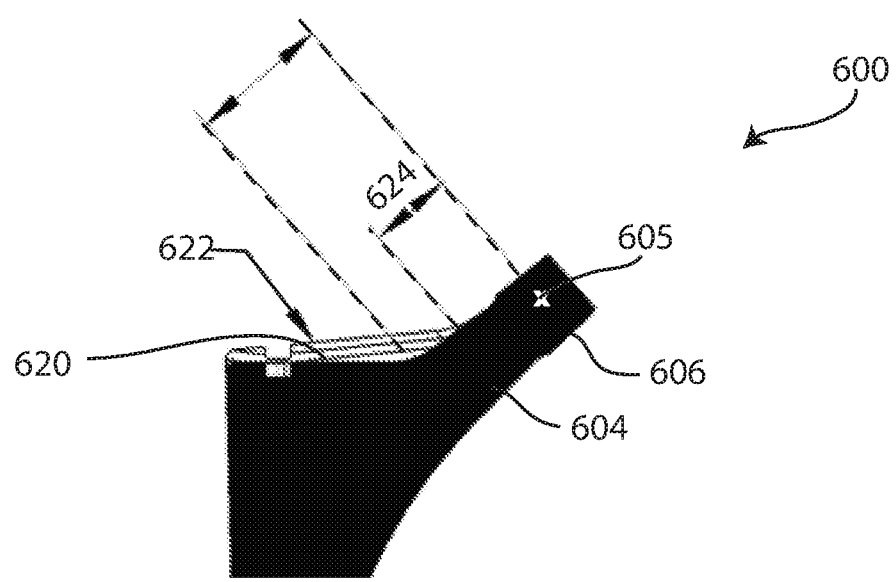
FIG. 9 is a side view of a proximal hip stem with a means for shortening the neck.
Figures 10A, 10B:
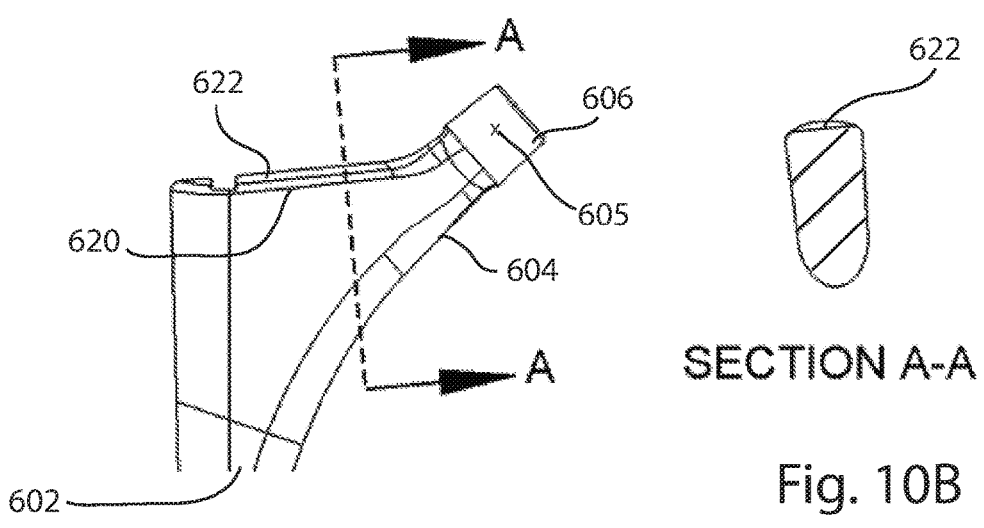
FIG. 10A is a side view of a proximal hip stem with a means for shortening the neck.
FIG. 10B cross section of the superior surface of the proximal hip stem with a means for shortening the neck.

Another example of a high impact femoral hip stem 600 may include a means for strengthening the neck. Referring to FIGS. 9 and 10A-10B, a proximal portion of femoral hip stem 600 is shown. It can be appreciated that stem 600 may include additional material deposited on the superior surface 620, relative to earlier designs, to create a rounded superior surface 622 that serves as a means for strengthening the neck. The addition of material to the superior surface to create a means for strengthening the neck may include material that is the same as the material used to fabricate the neck and stem portions, or may be a different material. FIGS. 10A and 10B provides a cross section A-A of the rounded superior surface 622, where additional material is present on the superior surface 620. Alternatively, the additional material may create a proximally elevated cross-section that is polygonal, rectangular or otherwise irregularly shaped.

The rounded superior surface 622 may serve to maintain a constant distance between the intended femoral head center location and the intersection of the lateral neck and the stem superior surface. This "effective neck length" 624 may remain approximately constant as the size of the overall implant is varied (stem diameter and offset). The additional material 620 may thus provide a constant, effective neck length 624, which is defined as the length between the intersection of the neck 604 and the additional material 620 and a center point of the head component 606. The porous coating 608 may also extend over the rounded superior surface 622.

The designs herein, such as that illustrated in FIGS. 9-10B, may be well adapted for prosthetic femoral heads larger than 22 mm, preferably larger than 32 mm, and preferably larger than 36 mm. Larger prosthetic heads may provide relatively greater range of motion than do smaller heads. The increased range of motion may be enjoyed on its own merits, or it may influence other choices in the overall design of a large-head total hip arthroplasty system. For example, instead of providing an actual increase in range of motion in the large-head system, the neck diameter or width may be augmented to improve its strength, a higher neck resection may be used, and/or a thinner acetabular component may be provided. A higher neck resection may permit the design to incorporate a higher level of porous coating, a shorter neck, and/or a medialized neck. While these choices may result in a large-head system whose range of motion is comparable to that of a small-head system, they may also result in a system whose strength and load transfer characteristics are better adapted for high demand patients.

Figures 11A, 11B:
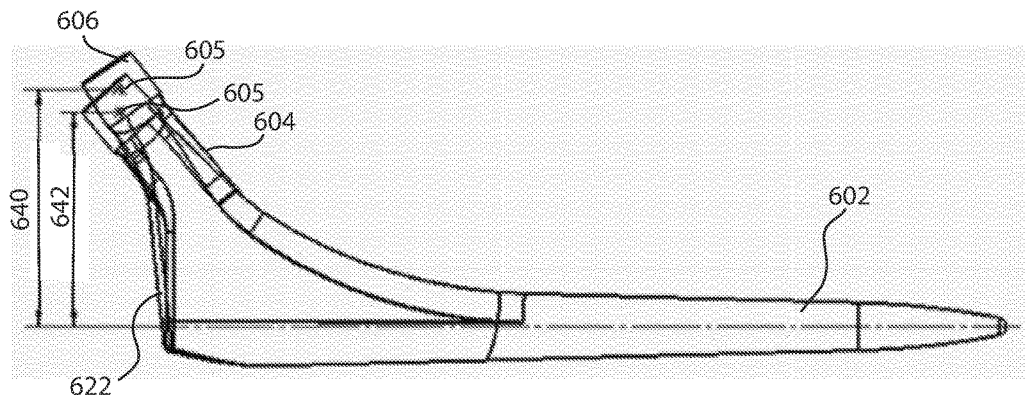
FIG. 11A is side view of a hip stem with two different possible offsets.
FIG. 11B is a table describing the geometric relationship between the diameter of the stem portion and the lateral offset.

Referring to FIGS. 11A and 11B, an additional example of the high impact femoral hip stem may combine the shortened neck length 604 described in FIG. 7 with the rounded superior surface 622 described in FIGS. 8 and 9, as a means for strengthening the neck. By combining these features, the neck may be strengthened enough such that the maximum femoral offset available for a given stem diameter or size may be increased. Specifically, this may be advantageous for patients with small intramedullary canal anatomy and large lateral offsets. This femoral morphology may be referred to as a "champagne flute" morphology. Referring to FIG. 11A, two different possible offsets are illustrated—a high offset 642, which may have lateral offsets comparable to the high offset offerings of standard stem designs, and a high offset plus 640 design, which may have increased lateral offsets.

The table presented in FIG. 11B presents an example of a geometric relationship between the diameter of the stem portion 602 and the lateral offset. The leftmost column of the table lists various distal stem diameters. The rightmost two columns present lateral offset values for the two designs. The rightmost column illustrates a 5 mm increase in lateral offset, although other increments are contemplated. For example, the high offset plus design may incorporate lateral offsets which are greater than one or two standard deviations above an average lateral offset for a patient population. Lateral offsets which are greater than three or more standard deviations above the average are also contemplated.

Figure 12A:
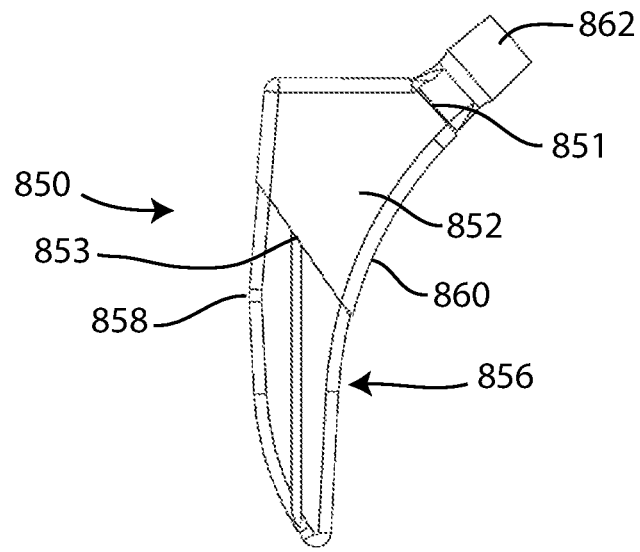
FIG. 12A is a front view of a hip stem with a shortened neck, high neck resection level and a shortened stem.
Figure 12B:
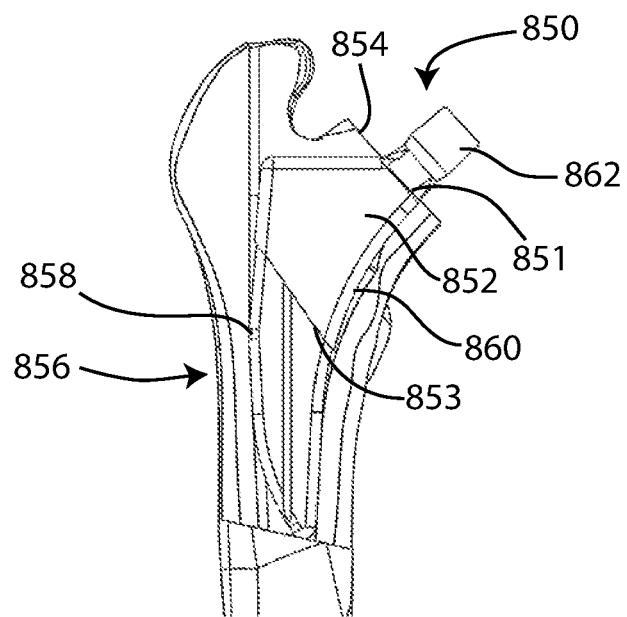
FIG. 12B is a front view of the hip stem of 12A inserted into a proximal femur.

Referring to FIGS. 12A-12B, an alternative embodiment of a high impact femoral hip stem with a shortened stem is illustrated. Femoral hip stem 850 may be similar to the hip stem described in FIGS. 6A and 6B, but may include a more proximal porous coating 852, a higher neck resection level 854, and thus, a shorter "effective neck length". Femoral hip stem 850 may include a shortened stem 856 with a trochanteric relief transition 858, and a medial curvature 860 with a continuous flare and gradual curvature. Femoral hip stem 850 may also include a head connecting feature 862, similar to previous embodiments described herein.

The shortened stem 856 may be less than 6 cm in length, or may be longer. The more proximal porous coating 852 may include a proximal boundary 851 and a distal boundary 853. The proximal boundary 851 of the more proximal porous coating 852 is illustrated to lie closer to the head connecting feature 862 than the proximal boundary 806 of the porous coating illustrated in FIGS. 6A and 6B. Also, the distal boundary 853 of the more proximal porous 852 coating may be located at or proximal to the trochanteric relief transition 858. By placing the distal boundary 852 of the more proximal porous coating 852 at this location, the implant may be more easily removed during a revision surgery, as the coating does not extend around the bend 858.

Further, when femoral hip stem 850 is inserted into a proximal femur, as illustrated in FIG. 12B, the neck resection level 854 is higher than the neck resection 814 shown in FIG. 6B. By shifting the neck resection level proximally, and thus shifting the porous coating proximally, subsequent revisions to the hip stem may become easier when compared to traditional hip stems with traditional porous coating levels. Also, similar to previous embodiments, the high neck resection level may allow for greater preservation of the natural femur, specifically in the calcar region, allowing the stem to share more of the load with the native femur and increasing the overall strength of the construct. Bony integration may be achieved closer to the prosthetic head. Because the porous coating is more proximal, and higher up on the medial flare, a greater compressive stress may occur in the bone at the interface, which may help to facilitate greater bone ingrowth. This may further reduce the unsupported length of neck. Overall, this may substantially prevent loosening of the stem in the femur, reduce migration of the stem within the femur, and provide greater implant stability.

Femoral hip stem 850 may also include a means for strengthening the neck, as described in previous embodiments.

Any of the stem components set forth herein may be fabricated from biocompatible materials. Examples of biocompatible materials include, but are not limited to, metals such as stainless steels, titanium and its alloys, cobalt-chrome-molybdenum alloys, and other chromium alloys; polymers such as polyetheretherketone (PEEK) and polyaryletherketone (PAEK); ceramics such as alumina and zirconia; and composites such as carbon fiber reinforced epoxy resin. Portions of a stem component may be fabricated from different materials according to the requirements of each portion. A stem component may be fabricated with a distal portion of one material and a proximal portion of another material. A stem component may be fabricated with a substrate of one material and a coating of another material. The material or materials may be solid (i.e., non-porous) or porous. The surface of a stem component may be smooth or rough on a micro- or macroscopic level. A stem component may be fabricated by casting, forging, machining, or a combination of methods. Castings may be applied by thermal, chemical, electrical, or comparable means. For example, coatings may be sintered, sputtered, vapor deposited, ion implanted, electroplated, and the like.

Any of the neck components set forth herein may be fabricated as described above for the stem components. Neck components may be preferably fabricated with materials, surface treatments, and methods of fabrication which enhance strength, or minimize unavoidable reductions in strength.

Figure 13A:
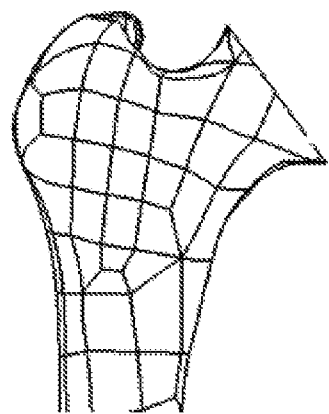
FIG. 13A is a cross section of a proximal femur that has been resected at the head neck junction.
Figure 13B:
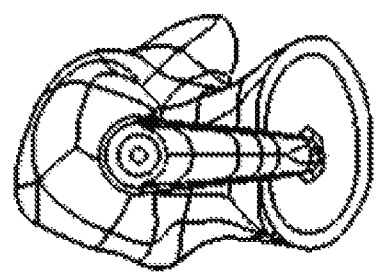
FIG. 13B is a top view of a proximal femur that has had the IM canal opened using a box chisel.

FIGS. 13A-13E illustrate steps in a method for preparing and inserting the high impact hip stem with a high final resection level. An osteotomy may be performed by removing the head to create a prepared resection surface at or near the head-neck junction as illustrated in FIG. 13A. The intramedullary (IM) canal may then be opened, using a box chisel or other comparable surgical instrument as shown in FIG. 13B.

Figure 13C:
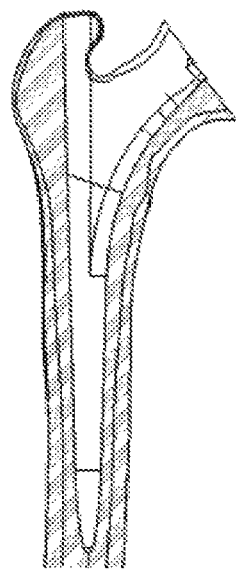
FIG. 13C is a cross section of a femur that has been broached.
Figure 13D:
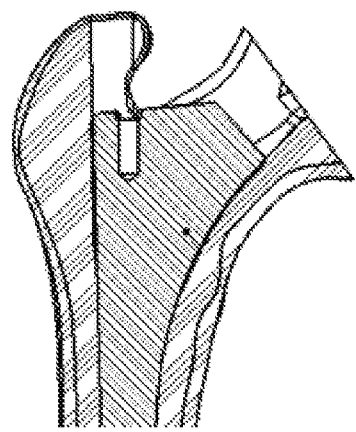
FIG. 13D is a cross section of a femur with an inserted broach, before final neck resection.
Figure 13E:
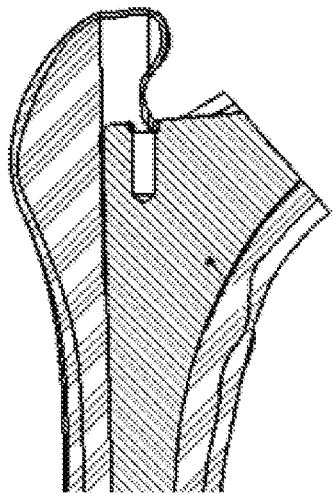
FIG. 13E is a cross section of the proximal femur and broach of FIG. 13D after final neck resection.

Once the IM canal has been opened, as shown in FIG. 13C the surgeon may then ream the distal IM canal and broach the proximal IM canal and proximal metaphysis, as illustrated in FIGS. 13D and 13E. Next, the neck resection may be completed using the broach as the resection guide for a planar calcar reamer or saw, FIG. 13E.

Figure 14A:
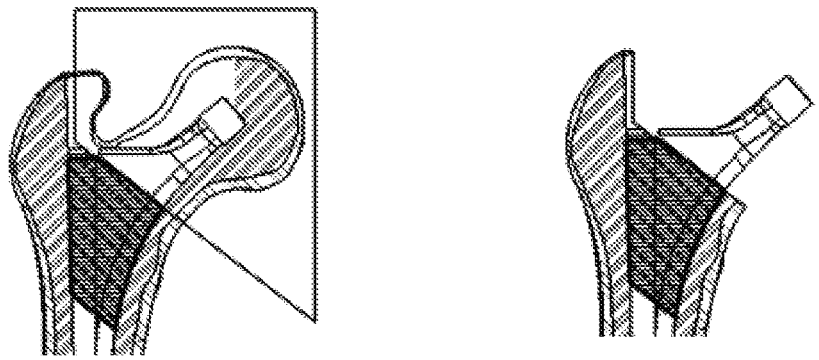
FIG. 14A is a cross section of a proximal femur with a traditional resection level and a stem with a traditional porous coating level.
Figure 14B:
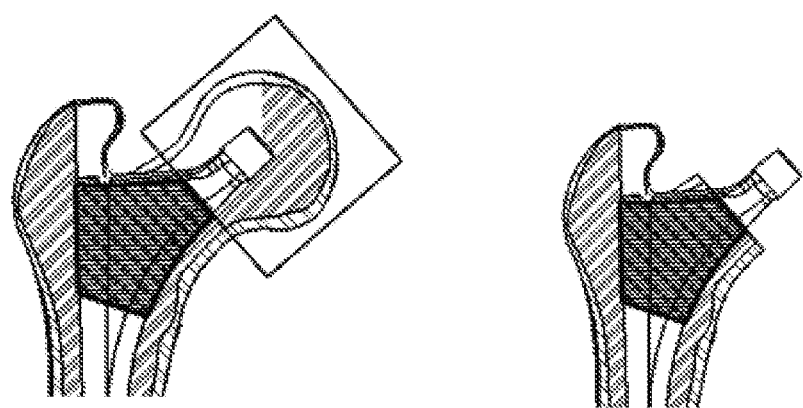
FIG. 14B is a cross section of a proximal femur with a high resection level and a stem with a high porous coating level.

FIGS. 14A and 14B provide a comparison between a traditional resection level (FIG. 124) and the final resection level according to the technique described in FIGS. 11A-11E. The final resection level (FIG. 14B) is higher on the femoral neck than traditional resectioning techniques, resulting in greater load sharing with native bone.

The high impact stem design described in FIGS. 7 and 9-11 may use the surgical technique described in FIGS. 13A-13E for greater bone preservation of the calcar region of the proximal femur during total hip arthroplasty, and thus enhanced load sharing. However, the increase in bone preservation potentially limits the patient's range of motion due to impingement.

Previous designs utilize a lower femoral neck cut and alter the implant neck geometry, including the incorporation of neck flats, to provide relief against acetabular component impingement when using smaller head sizes. When using larger head sizes, this same geometry alteration can be made in the surrounding bone, for example, by using chamfer cuts, relief, rounding, edge break, or other modifications in the zone of potential impingement. Chamfer cuts or other cuts made in the surrounding bone may provide relief where impingement will occur against the acetabular component. This may allow for a thicker implant neck geometry to be used, since impingement relief is addressed in the bone and not the implant. Any method can be used to alter the bony geometry to this effect, including removing portions of bone to reveal chamfered, planar surfaces. Some proximal bone may be retained for load sharing in a high impact application, such as a bony "shelf" to help transfer load from the neck portion of an inserted hip stem. Alternative bone surface geometries may include a rounded surface, an L-shaped cut-out or otherwise contoured surface resection geometry.

Figure 15C:
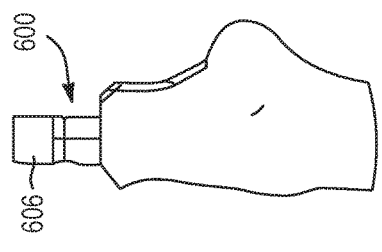
FIG. 15C is a superior front view of a chamfered bone section with a lower resection level.
Figure 15D:
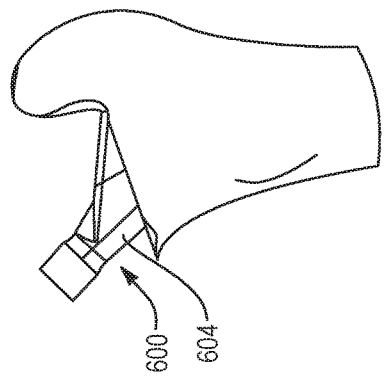
FIG. 15D is a front view of a chamfered bone section with a lower resection level.
Figure 15A:
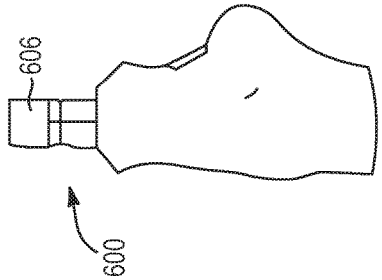
FIG. 15A is a superior view of a chamfered bone section with a high resection level.
Figure 15B:
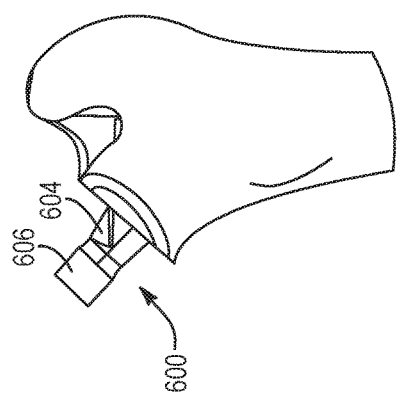
FIG. 15B is a front view of a chamfered bone section with a high resection level.

FIGS. 15A and 15B illustrate an example of a chamfered bone section that may be used in conjunction with the high impact hip stem that has previously been described. The chamfered bone surfaces shown in FIGS. 15A and 15B may maintain a high level of calcar bone, while allowing for a typical range of motion. FIGS. 15C and 15D illustrate another example of a chamfered bone, in which the resection surface is more angulated, while still retaining a high level of calcar bone, and also allow for a typical range of motion.

Figure 16B:
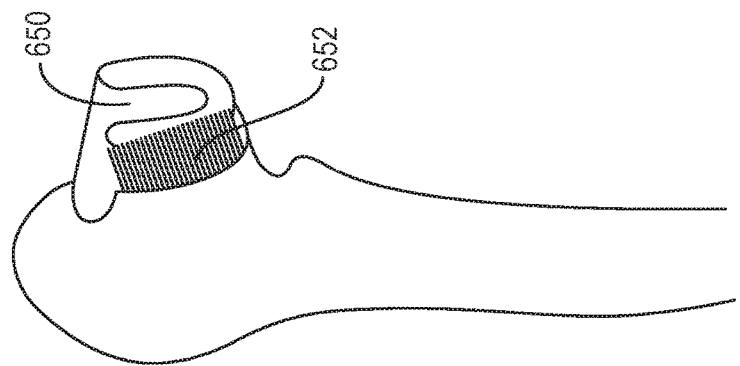
FIG. 16B is an isometric view of the proximal femur of FIG. 16A, with a shaded area indicating bone to be removed to form a chamfered anterior edge.
Figure 16A:
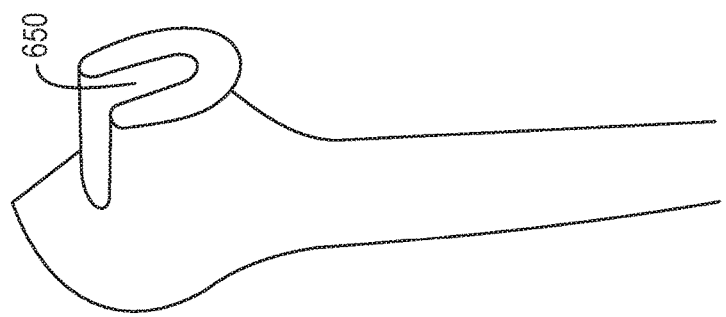
FIG. 16A is an isometric view of a proximal femur with a high resection level that has been broached.
Figure 16C:
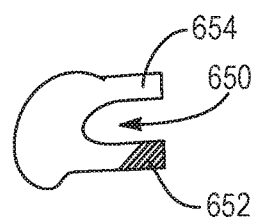
FIG. 16C is a top view of the proximal femur with a high resection level and a chamfered anterior edge.
Figure 16D:
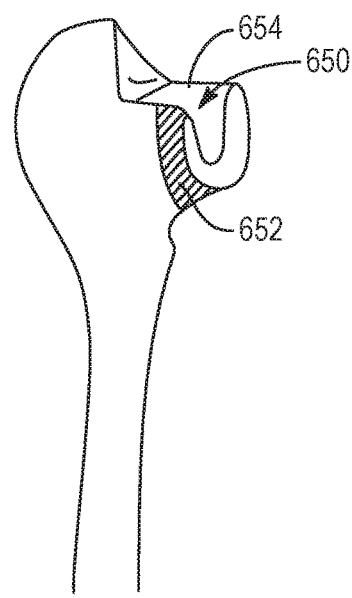
FIG. 16D is a proximal femur with a high resection level and a chamfered anterior and posterior edge.
Figure 16E:
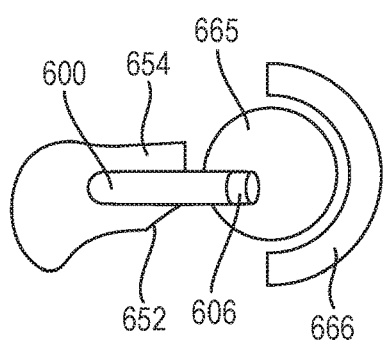
FIG. 16E is a top view of a proximal femur with a high resection level and chamfered anterior edge, with a hip stem and a head.
Figure 16F:
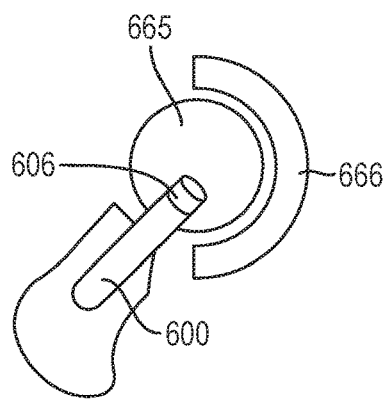
FIG. 16F is a top view of a rotated proximal femur with a high resection level and chamfered anterior edge, with a hip stem and acetabular cup inserted.

FIGS. 16A-25B illustrate instruments and methods that may be used for creating the chamfered surfaces to reduce impingement and allowing for a hip stem with a strengthened neck. FIGS. 16A-16F illustrate additional steps to further prepare the anterior calcar chamber to increase range of motion and to prevent possible impingement of the prosthetic components and/or host bone. FIG. 16A illustrates a proximal femur that may have been prepared according to the technique of FIGS. 13A-13E. A portion of the femoral head has been removed to reveal a horse-shoe shaped cavity 650 that may allow for access to the IM canal. The depth and width of the cavity may be variable, according to the patient's anatomy. Alternatively, the cavity may be rectangular or irregularly shaped. In FIG. 16B, the proximal femur has been further prepared by introducing a beveled or chamfered anterior edge 652 to the cavity 650. FIG. 16C provides a top view of the cavity 650, which may include a first, non-beveled posterior edge 654 and a beveled anterior edge 652. Alternatively, both the anterior and posterior edge may be beveled. In this case, the posterior and inferior bone stock may be preserved for maximal stress transfer, as illustrated in FIG. 16D. When the anterior edge is beveled, the range of motion may be enhanced, as shown in FIGS. 16E and 16F. Referring to FIGS. 16E-16F, a top view of a proximal hip stem inserted into a femur through the cavity 650 is shown, with the head connecting component 606 connected to a modular head 665, which is received by an acetabular cup 666. The implanted hip stem may be the hip stem 600 described in previous examples. FIG. 16E illustrates the hip stem 600 and connected modular head 665 in a neutral, non-rotated position. FIG. 16F illustrates the hip stem 600 and connected modular head 665 rotated such that the anterior, beveled edge 452 of the cavity 450 comes into contact with the acetabular cup 666. It can be seen that the beveled edge 652 reduces the potential for impingement by allowing the proximal femur and to rotate further before contacting the anterior edge of the acetabular cup 666.

Figure 17A:
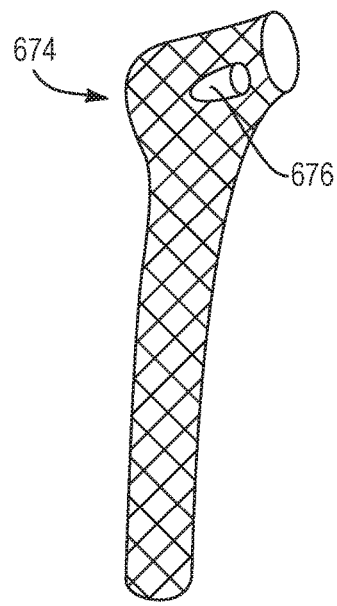
FIG. 17A is a side view of a broach that includes a mating feature for guiding a reamer along a trajectory to create a chamfer on the bone.
Figure 17B:
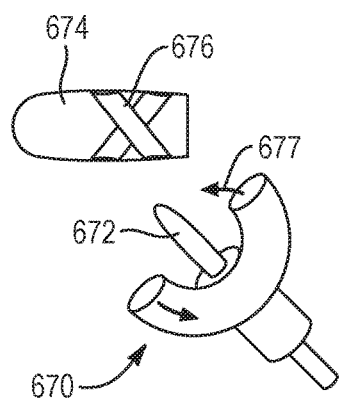
FIG. 17B is a side view of a planar reamer and a broach.
Figure 17C:
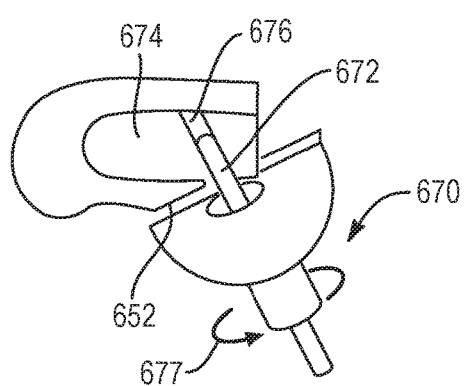
FIG. 17C is a side view of a planar reamer engaged with a broach.

Referring to FIGS. 17A-17C, a beveled anterior edge 652 may be prepared by using a planar reamer 670, sometimes referred to as a calcar planer or calcar reamer, on a post 672 engaged with a broach 674. FIG. 17A shows a broach 674. The broach includes an oblique proximal hole 676 which is perpendicular to the desired angle of the beveled anterior edge 652. With the broach 674 fitted into the proximal femur, the post 672 is inserted into the hole 676 to align the reamer 670 with the hole. As the reamer 670 rotates, as indicated by motion arrows 677 and advances, it cuts away the proximal anterior edge to form the bevel 652. The reamer 670 may include a central cavity sized and shaped to receive a proximal anterior corner or shoulder of the broach without interference while the reamer is spinning.

The broach may include only one hole, in which case separate right and left broaches may be provided. The broach may also include two holes so that a single broach is suitable for right and left femurs.

Figure 18A:
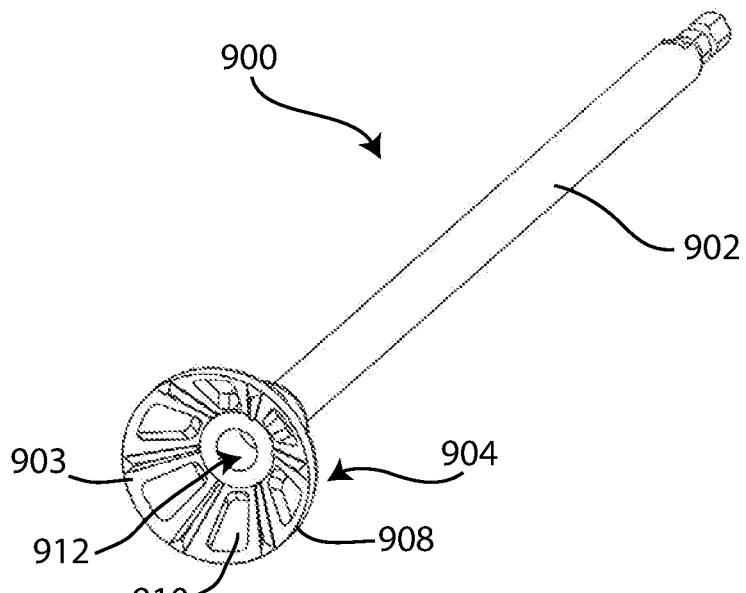
FIG. 18A is a bottom perspective view of a chamfered reamer with a cup-shaped cutting feature.

Referring to FIGS. 18A-20B illustrate another example of a method and instrument that may be used to prepare a femoral hip stem for a hip prosthesis with a high resection level, while retaining a normal range of motion in a patient. Referring to FIGS. 18A and 18B, a chamfered reamer is shown. Chamfered reamer 900 includes an elongated handle portion 902, connected to a cup-shaped cutting surface 904. The cup-shaped cutting surface may also be referred to as a bone cutting surface. The cup-shaped cutting surface 904 may be conical, or include varying degrees of curvature. The elongated handle portion 902 is connected to the cup-shaped cutting portion 904 at a shoulder 906. The shoulder 906 may have a greater diameter than the elongated handle 902. The cup-shaped cutting portion 904 may be located distal to the shoulder 906, and may flare outwards. The cup-shaped cutting portion 904 may include an inner surface 903, and an outer surface opposite 905 of the inner surface 903. The cup-shaped cutting portion 904 may include a sharpened edge portion 908 at the intersection of the inner 903 and outer surfaces 905. The cup-shaped cutting portion 904 may include a plurality of apertures 910, which may also be referred to as windows, which may include sharpened edges 911 that facilitate removal of bone. The window edges 911 may otherwise be flattened or rounded. At the apex of the cup-shaped cutting portion 904, the chamfered reamer 900 may include a female feature 912 shaped to receive a portion of a post that is connected to a broach. The female feature 912 may include a socket, or hole, that extends from the inner surface 903 of the cup-shaped cutting portion 904 into the shoulder 906. The mating feature 912 may otherwise be a complementary male feature shaped to be received by a groove or socket in a broach.

Figure 18B:
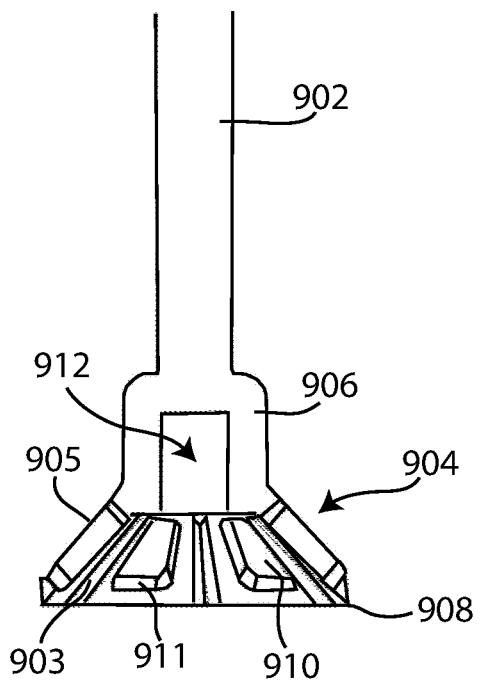
FIG. 18B is a cross section of the chamfered reamer of FIG. 18A.
Figure 19A:
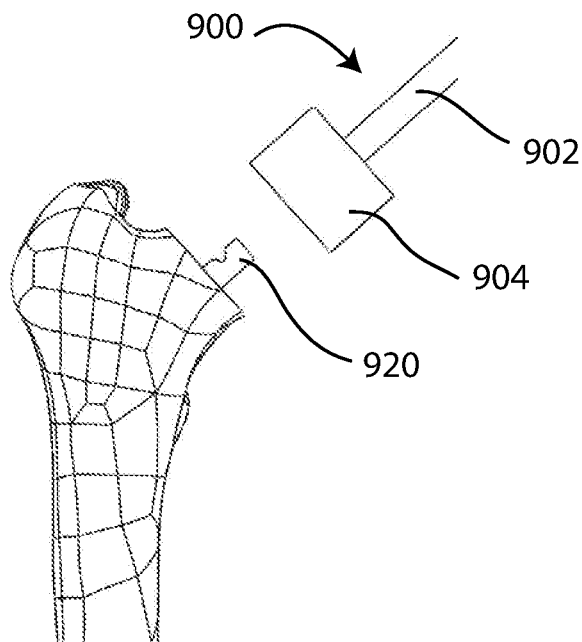
FIG. 19A is a front view of a proximal femur with an inserted broach and protruding post.
Figure 19B:
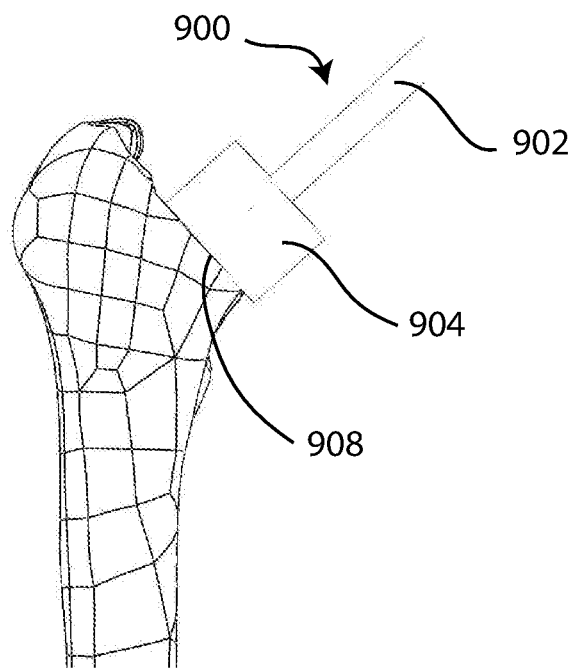
FIG. 19B is a front view of a chamfered reamer engaged with the broach of FIG. 19A.

Referring to FIG. 19A, a broach with a post 920 is shown inserted into a proximal femur, after the head of the proximal femur has been resected at the head-neck junction. The broach may have been inserted into the femoral cavity until the broach is flush with the resection level, and the post is oriented such that it extends substantially normal to the resection plane. The chamfered reamer 900 described in FIGS. 18A and 18B is shown mating with the inserted broach in FIG. 19B. When the chamfered reamer 900 is engaged with the broach post 920, the sharpened edge portion 908 may lie flush with the resection plane. The instrument 900 may then be actuated to ream the calcar section by rotating and applying force to the chamfered reamer to remove bone tissue.

Figure 20A:
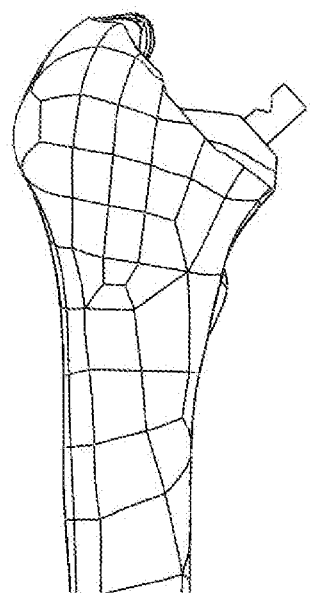
FIG. 20A is a front view of a proximal femur with an inserted broach and protruding post after the calcar region has been reamed using a chamfered reamer.
Figure 20B:
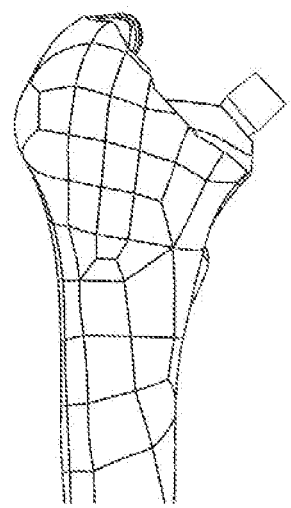
FIG. 20B is a front view of a proximal femur that has been reamed using a chamfered reamer and a hip stem has been inserted.

Referring to FIG. 20A, a proximal femur is shown after it has been reamed using the chamfered reamer 900, with the broach 920 still implanted in the proximal femur. After reaming, the broach may be removed and a femoral hip prosthesis, such as those previously described, may be inserted, as illustrated in FIG. 20B.

Another example of a calcar reamer may include a central aperture shaped to receive a proximal portion of a broach that has been inserted into a proximal femur. The structure and method of use of the calcar reamer may be similar to the reamers shown in FIGS. 17A-20C and, although the calcar reamer may include at least one chamfered cutting surface, such that as the reamer is rotated, the chamfered cutting edge acts in a saw-like capacity to create a complimentary chamfered bone surface on one or both sides of the broach. These instruments may include a variety of cutting edge geometries to create differently shaped bone resections. Alternatively, a resection may be done free-handed to remove bone portions surrounding the hip stem and reduce potential infringement.

Figure 21A:
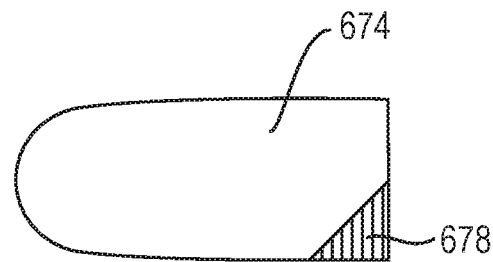
FIG. 21A is a superior view of a broach with a beveled edge.
Figure 21B:
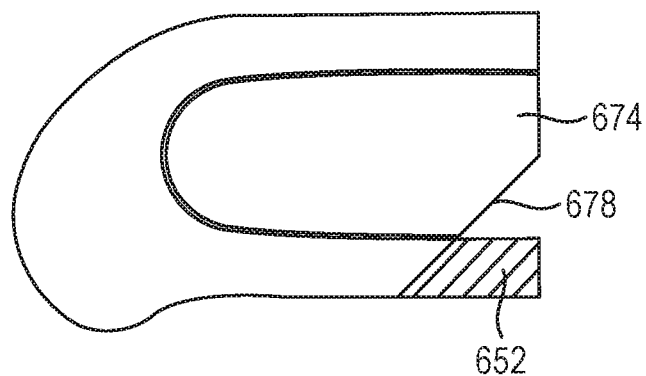
FIG. 21B is a top view of a broach with a beveled edge inserted into a proximal femur cutout with a beveled anterior edge.
Figure 22A:
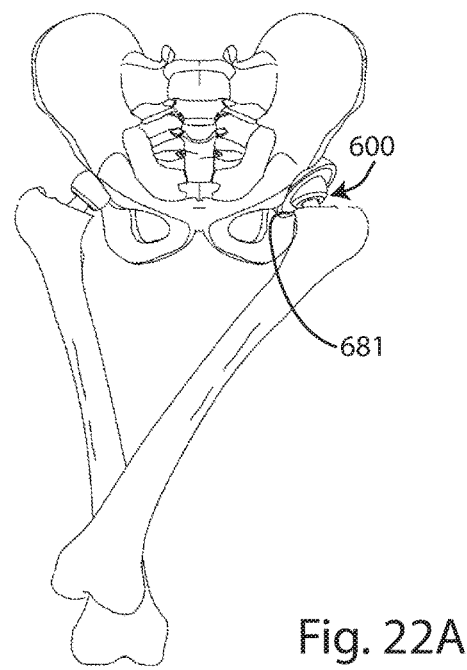
FIG. 22A is a front view of a femur with a hip stem with a modular head mated with an acetabular cup and liner in a pelvis.
Figure 22B:
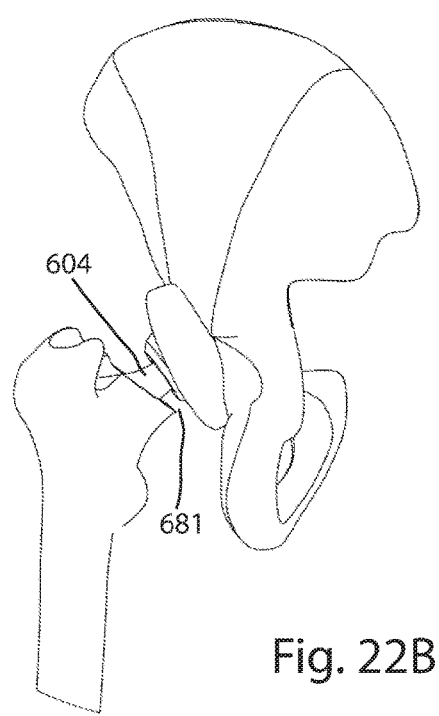
FIG. 22B is a front view of a hip stem with a modular head inserted into an acetabular liner, where there is impingement between the bone and the acetabular implant.

FIGS. 21A-21B illustrate another arrangement for preparing the beveled anterior edge 652 by using a saw guided by a beveled edge 678 of a broach 674. In this example, the proximal anterior corner of the broach carries a beveled portion 678 which establishes the desired resection plane for the beveled anterior edge 652. With the broach 676 fitted into the proximal femur, the saw is aligned with and moved along the beveled portion 678. As the actuated saw advances, it cuts away the proximal anterior edge to form the bevel 652.

The broach may include one or two beveled portions 678.

FIGS. 22-27 illustrate another example of an instrument and method that may be used for preparing the proximal femur during total hip arthroplasty to minimize the potential for impingement and maintain the patient's natural range of motion. FIGS. 22A and 22B illustrate a prosthetic femoral hip stem connected to a modular head inserted into a femur. The hip stem may be the high impact hip stem 600 described previously in this application. Referring to FIGS. 22A and 22B, no chamfer resection cuts have been performed after the hip stem 600 was inserted into the femur. The connected modular head portion can be seen to interface with an acetabular component. It can be seen in FIG. 22B that without chamfer resection cuts, there may be posterior impingement 681 of the joint at the bone-acetabular cup interface, thus limiting the patient's range of motion.

FIGS. 23-27 illustrate a chamfer cutting guide 700 that may be fitted or otherwise attached to the proximal portion of a broach 674 that has been inserted into the proximal femur, and may be used to create chamfered edges in the native femur that reduce impingement of the prosthetic head against the anterior and posterior portions of the natural femur.

Figures 23A, 23B:
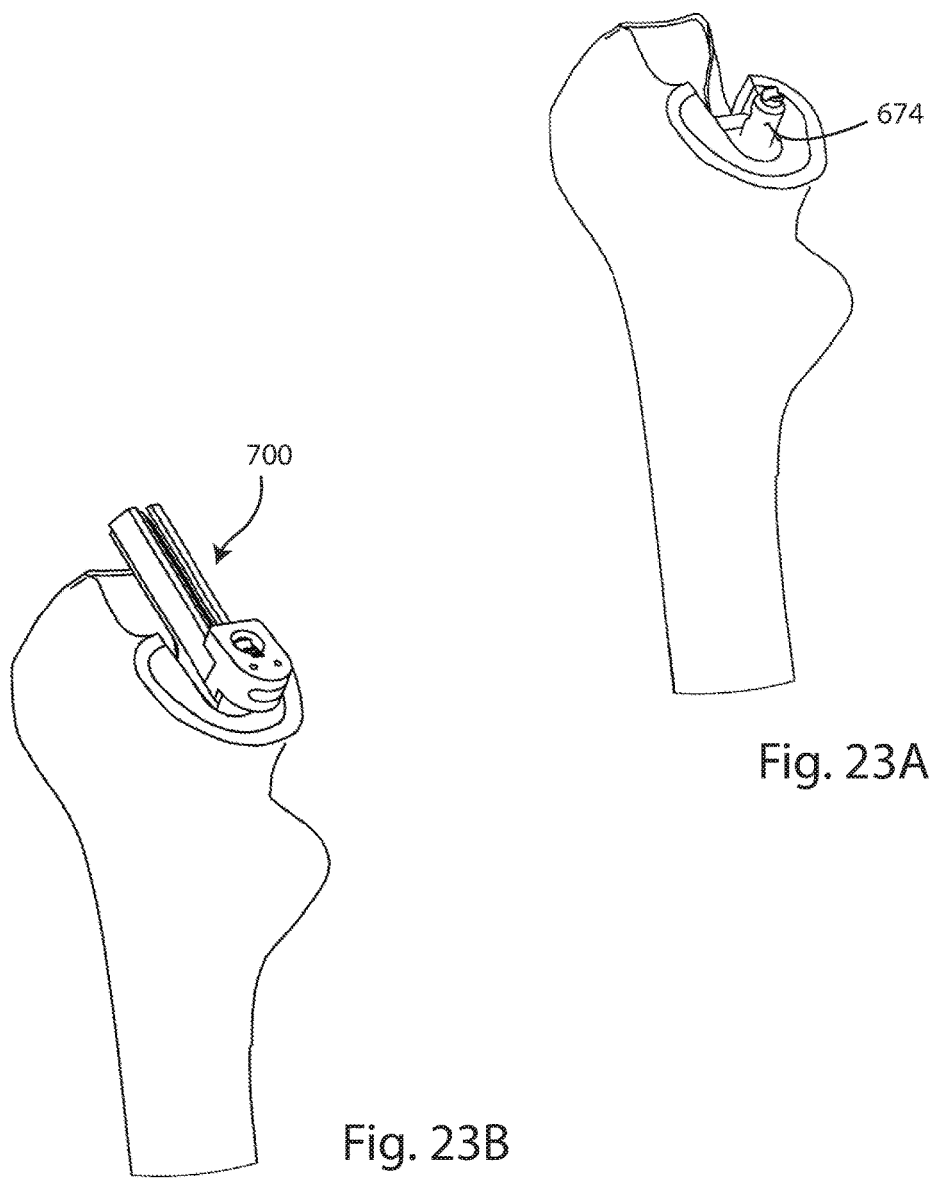
FIG. 23A is a top perspective view of a broach inserted into a proximal femur.
FIG. 23B is a top perspective view of a chamfer cutting guide attached to a broach inserted into a proximal femur.

Referring to FIG. 23A, a broach 674 is shown inserted into the proximal femur. The broach 674 may be inserted into the proximal femur using a method similar or identical to the process described previously in this application. FIG. 23B illustrates a chamfer-cutting guide 700 that may be attached to a proximal portion of the broach 674.

Figure 24:
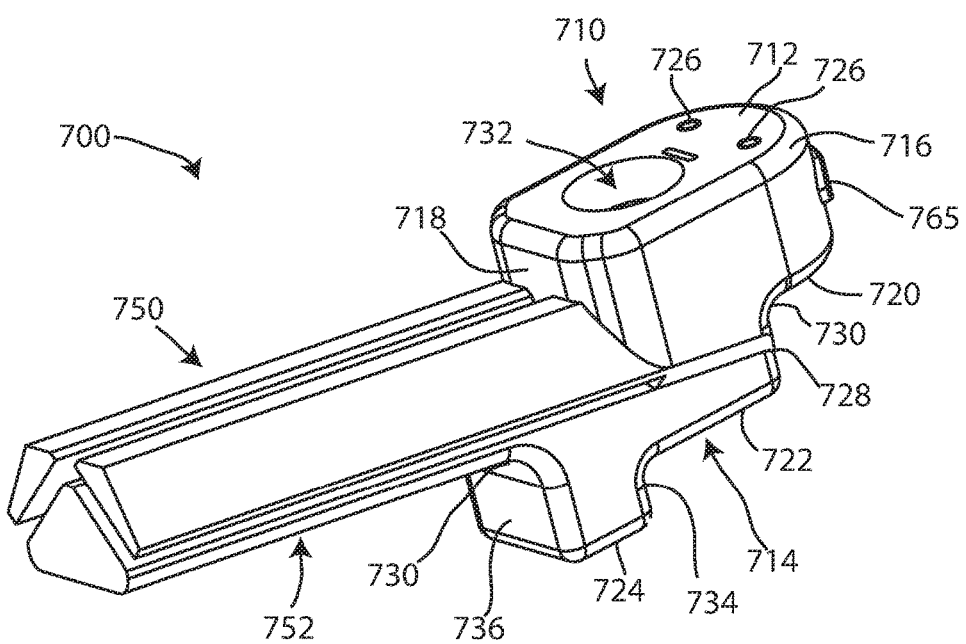
FIG. 24 is a top perspective view of a chamfer cutting guide.

FIG. 24 provides a perspective view of chamfer cutting guide 700, which may include a first portion 710, which may be referred to as an engagement portion and a second portion 750, which may be referred to as a guide portion. The engagement portion 710 may act to secure chamfer cutting guide 700 to a broach 674 or other anchor feature in bone, and may include a proximal surface 712, and a distal broach contacting portion 714 opposite the proximal surface. The proximal surface 712 may extend between a rounded edge 716 and a guide portion interface 718.

Figure 25:
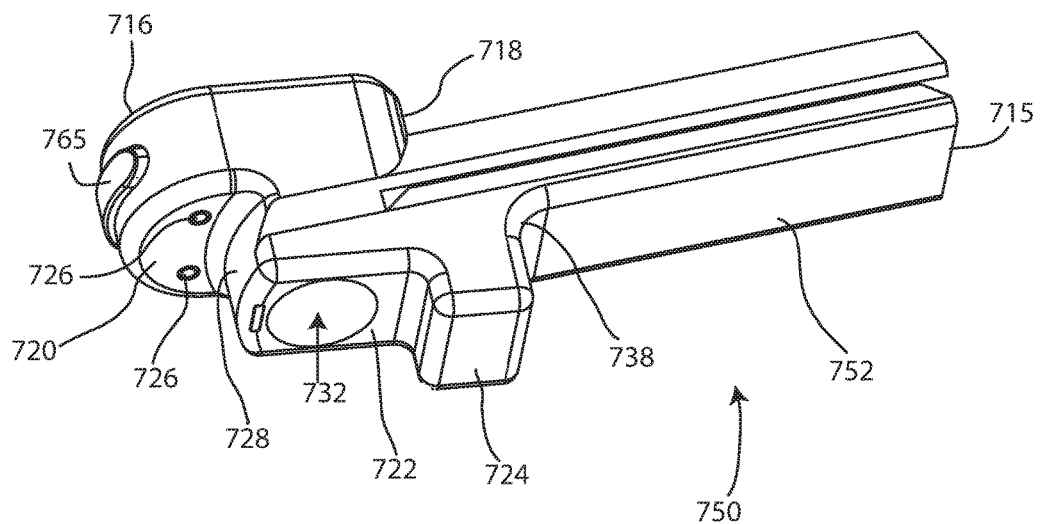
FIG. 25 is a bottom perspective view of a chamfer cutting guide.

The distal broach contacting 714 portion, as illustrated in FIG. 25, may have a step-like configuration, and include a first step 720, a second step 722 that is offset distally from the first step 720 and a third step 724 that is offset distally from the second step 722. The number and orientation of steps may be variable. The distal broach contacting surface 714 may also include various alternative configurations shaped to interface with the bone portion surrounding the inserted broach, specifically, the bone-contacting portion may interface with the bone on the interior portion of the cavity 650 described in FIGS. 16A and 16B. Alternative configurations may include a flat, sloped, or otherwise contoured surface to match the surface geometry of the patient's bone.

The surface of the first step 720 on the distal broach contacting portion 714 may include at least one aperture 726, and in this case, includes two relatively small and substantially circular apertures.

The first step 720 and second step 724 may be connected by a first vertical surface 728, which may intersect the first step 720 at a rounded concave corner 730. The corner may otherwise by sharp, beveled, coved or eased. The second step 724 may include at least one larger aperture 732, as shown best in FIG. 25. The larger aperture 732 shaped to receive a proximal portion of a broach. The aperture 732 may extend entirely through the engagement portion 710 to intersect the proximal surface 712.

When the chamfer-cutting guide 700 is attached to the broach 674, a central axis of the aperture 732 may align with the axis of the femoral neck. The chamfer-cutting guide 700 may engage the broach 674 via a spring loaded mechanism, which may be activated by pressing on a button 765 or lever. When button 765 becomes depressed, the larger aperture 732 of chamfer guide 700 may become able to slide over the proximal portion of the broach. When the external force on the button 765 is released, the spring force may push a side portion of the larger aperture 732 rigidly against the broach post, thus compressing it against the side of the larger aperture 732. This may rigidly lock the cutting guide 700 into place. The engagement portion 710 may include additional apertures or connecting features to secure the chamfer-cutting guide 700 during use. Examples of additional connecting features may include a protruded portion, a morse-taper or other male, or female, connecting features.

The second step 722 and third step 724 may be connected by a second vertical surface 734. The third step 726 may intersect the second vertical surface 734 and a third vertical surface 736 that is opposite the second vertical surface 734. The third vertical surface 736 may connect to a second rounded corner 738, where it intersects a distal surface 752 of the guide portion 750.

Figure 26:
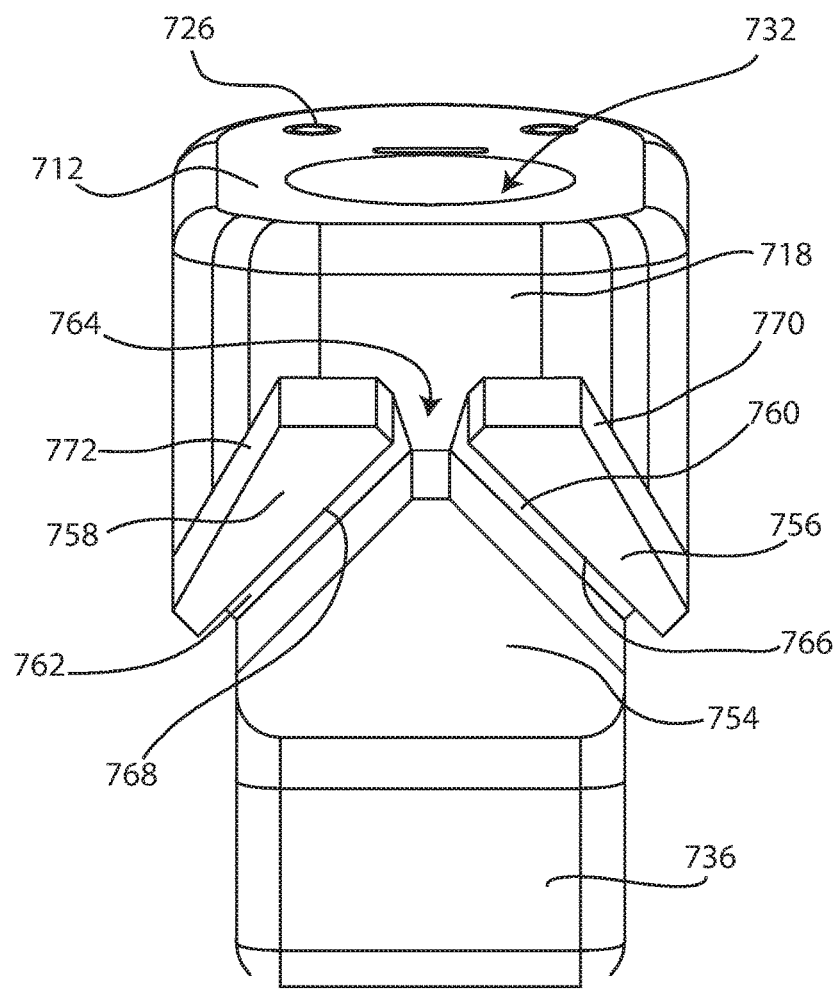
FIG. 26 is a side view of a chamfer cutting guide.

A bottom perspective view of chamfer cutting guide 700 is shown in FIG. 25. The guide portion 750 may be substantially elongated and generally rectangular in shape. The guide portion 750 may include a distal surface 752 that is substantially rectangular. The distal surface 752 may extend between the engagement portion 710 and a flat end portion 715. A cross-section of guide portion 750 is illustrated in FIG. 26. The cross section of guide portion 750 is shown to be generally triangular and contains a central body 754 that may be an equilateral triangle, and two appendages 756, 758 that sit superior and have interior edges 766, 768 that are parallel to the edges of the triangular body 754. The space between the appendages 756, 758 and the edges of the triangular body 754 make up channels or slots 760, 762 that act as cutting guides to establish a predetermined cutting trajectory for a traditional surgical saw or other surgical cutting instrument. The two cutting guides 760, 762 may act as an anterior slot and a posterior slot for creating the desired resulting bone resection on both anterior and posterior sides of the proximal femur. The two slots 760, 762 may intersect at a proximal primary channel 764 that extends along the length (of the z-axis) of the central body 754, as illustrated in FIG. 27A.

The appendages 756, 758 may have exterior surfaces 770, 772 that serve as secondary cutting guides that allow for greater surgeon flexibility. The flat exterior surfaces 770, 772 create additional guiding interface that a powered saw can rest on while creating an alternate bone resection.

Figures 27A, 27B:
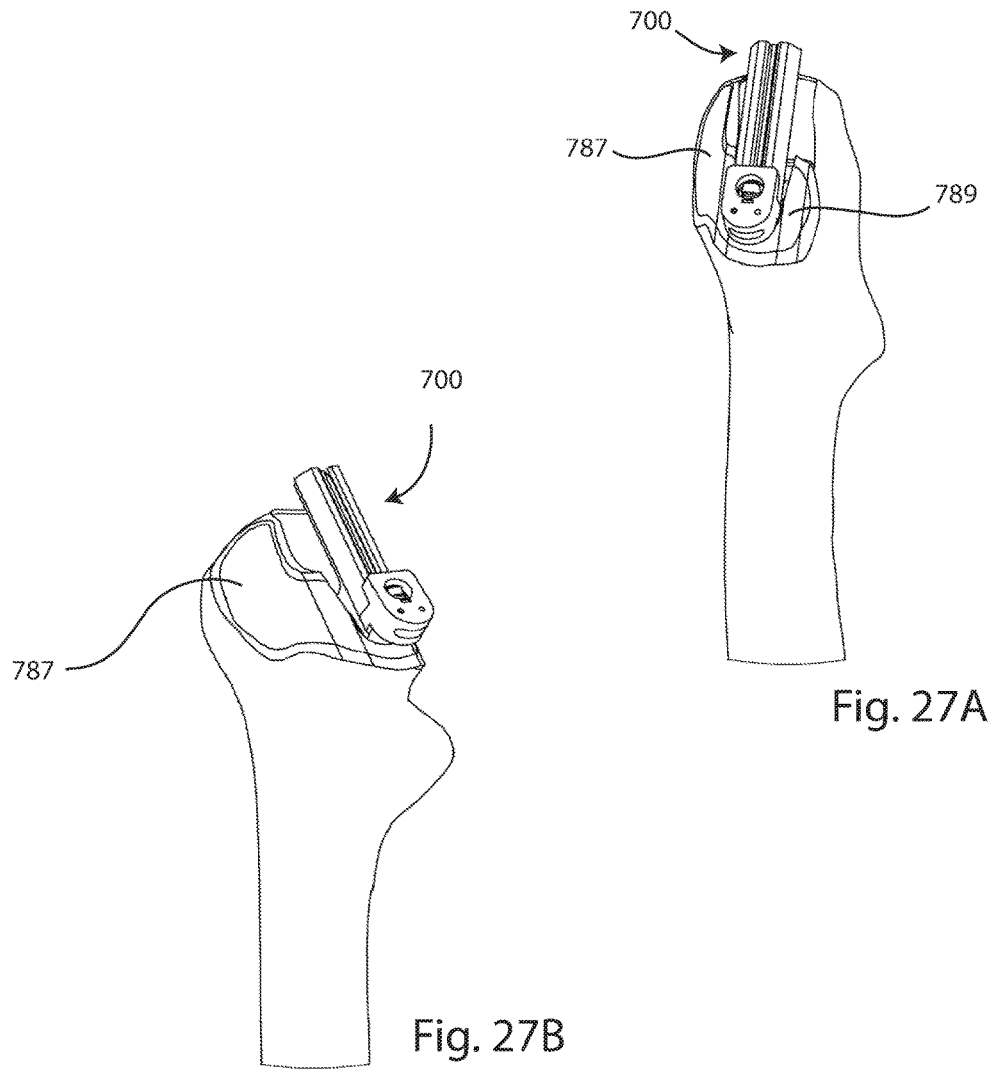
FIG. 27A is a top view of a chamfer cutting guide attached to a broach inserted into a femur and a chamfered bone surface.
FIG. 27B is a top perspective view of a chamfer cutting guide attached to a broach inserted into a femur and a chamfered bone surface.

Referring to FIGS. 27A-27B a proximal femur is shown with an attached chamfer cutting guide 700 after anterior and posterior resections that were performed using the cutting guide 700. The resultant geometry post-resection creates flat surfaces 787, 789 on anterior/posterior surfaces of the femur. This is similar in nature to the design of a traditional hip stem that includes flat surfaces on the anterior/posterior sides of the neck to avoid impingement with the cup and liner.

Figure 28:
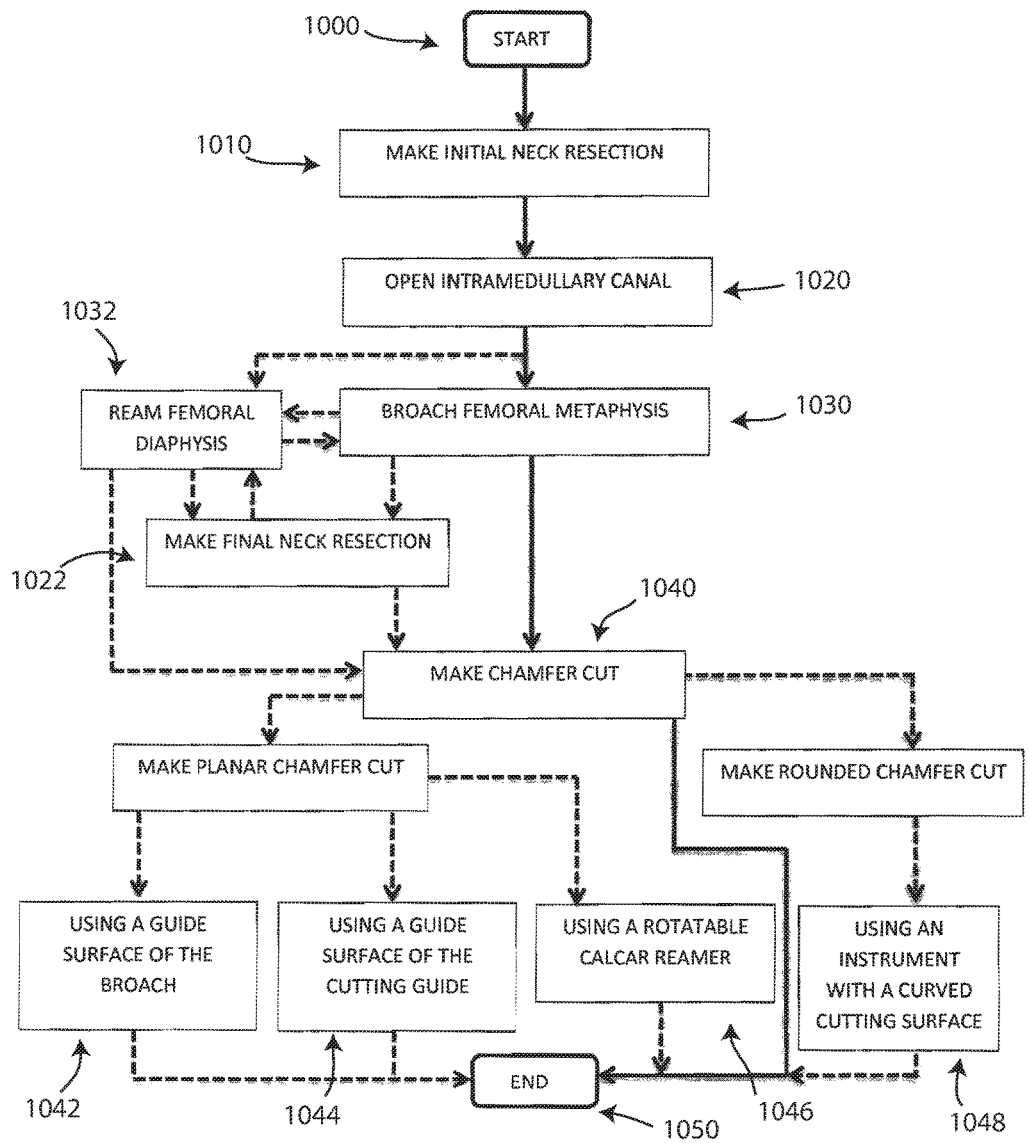
FIG. 28 is a diagram illustrating methods of preparing anterior and/or posterior chamfer cuts.

Referring to FIG. 28, a diagram illustrates methods of preparing a femur with anterior and/or posterior chamfer cuts. The method starts with step 1000, although it is appreciated that this method may occur after another method, such as a method for establishing a surgical approach to a hip joint. In step 1010, an initial neck resection is made by removing the femoral head at or near the head-neck junction, or in a subcapital region of the femoral neck. The intramedullary canal is then opened in step 1020. In step 1030, the proximal metaphysis is then broached. Progressively larger broaches may be used sequentially in step 1030. The broach may be positioned in the proximal femur such that it is flush with the resection level. Referring to step 1040, one or more chamfer cuts are made at one or more locations (anterior, posterior, medial) around the neck resection. At this point, the method ends with step 1050, although it is appreciated that this method may occur before another method, such as a method for implanting a prosthetic hip stem.

In optional step 1022, a final neck resection may be made with reference to the final broach in its final position in the proximal femur. Step 1022 may occur after step 1030.

Referring to optional step 1032, the distal intramedullary canal, or diaphysis, may be reamed before or after steps 1022 and/or 1030. Progressively larger reamers may be used sequentially in step 1032.

Steps 1042, 1044, and 1046 describe various possible techniques and instruments that may be used for creating planar chamfer cuts. Referring to step 1042, a planar chamfer cut may be made with reference to a guide surface of the broach, similar to the system described in FIGS. 21A-21B. Referring to step 1044, the planar chamfer cut may alternatively be made with reference to a guide surface of a cutting guide, such as the cutting guide described in FIGS. 24-27B. Referring to step 1046, the planar chamfer cut may also be made with a calcar reamer, such as the calcar reamer described in FIGS. 17A-17C, or with a saw. Referring to step 1048, a curved chamfer cut may be made with reference to the broach using a curved chamfer cutting guide surface, such as that described on the instrument illustrated in FIGS. 18A-19B.

The high impact femoral hip stem incorporates neck-strengthening adaptations, such as the shorter neck length and wider neck diameter, which improve the stem's ability to sustain dynamic loads in service. The stem also incorporates stress-transfer adaptations, such as a higher, medialized resection level and porous coating level, which improve the stem's ability to transfer stress to the calcar region of the femoral neck. The stem features a pronounced medial flare which also aids in stress transfer by increasing the projected area of the stem when viewed along the stem axis. Because the stem transfers more stress to the calcar region, the stress distribution in the remainder of the femur may better approximate that of the natural femur, thus preserving more bone substance over a longer period of time.

What is claimed is:

1. A femoral hip prosthesis configured to be implanted into a resected proximal end of a femoral bone and configured to receive a femoral head, comprising:
   a stem including a center longitudinal axis and a proximal end;
   a neck defining a neck axis intersecting with the center longitudinal axis, the neck including a base neck portion and a proximal neck portion, the proximal neck portion extending proximally from the base neck portion to a head connecting feature having a center point, the head connecting feature having structure for receiving the femoral head, the center point located within or along the structure for receiving the femoral head, the proximal neck portion extending with a first length oriented along the neck axis to define a lateral extent, the neck extending relative to the stem to define a lateral offset distance, the lateral offset distance defined laterally between the center longitudinal axis of the stem and the center point of the head connecting feature;
   a superior surface extending between the base neck portion and the stem to blend the base neck portion and the stem together; and
   an exterior coating having a proximal boundary extending adjacently parallel along the superior surface and extending distally over a portion of the stem, the proximal boundary extending distally at an angle to define an angled proximal boundary to cover the base neck portion of the neck, the angled proximal boundary positioned to define the proximal neck portion such that the first length of the lateral extent of the proximal neck portion is defined from the angled proximal boundary of the exterior coating to the center point of the head connecting feature;
   wherein the first length of the lateral extent ranges from 20% to about 50% of the lateral offset distance.

2. The prosthesis of claim 1, wherein the superior surface extends along a transverse plane that intersects the proximal end of the stem and the base neck portion of the neck.

3. The prosthesis of claim 1, wherein the exterior coating is porous.

4. The prosthesis of claim 1, wherein the exterior coating is porous and is configured to enhance biological growth.

5. The prosthesis of claim 1, wherein the first length of the lateral extent ranges from 20% to 40% of the lateral offset distance.

6. The prosthesis of claim 1, wherein the first length of the lateral extent ranges from 20% to 30% of the lateral offset distance.

7. The prosthesis of claim 1, wherein the angled proximal boundary of the exterior coating is configured to correspond and align with the resected proximal end of the femoral bone.

8. The prosthesis of claim 1, wherein the exterior coating is configured to enhance bone ingrowth.

9. The prosthesis of claim 1, wherein the superior surface comprises a rounded surface.

10. The prosthesis of claim 1, further comprising a prosthetic head configured to be coupled to the head connecting feature.

11. A femoral hip prosthesis configured to be implanted into a resected proximal end of a femoral bone and configured to receive a femoral head, comprising:
    a stem including a center longitudinal axis and a proximal end;
    a superior surface extending transversely relative to the center longitudinal axis from the proximal end of the stem;
    a neck defining a neck axis, the neck extending proximally from the superior surface such that the superior surface blends the stem and a base of the neck together, the neck extending proximally to a head connecting feature having a center point, the head connecting feature having structure for receiving the femoral head, the center point located within or along the structure for receiving the femoral head, the neck having a first length oriented along the neck axis to define a lateral extent, the neck extending relative to the stem to define a lateral offset distance, the lateral offset distance defined laterally between the center longitudinal axis of the stem and the center point of the head connecting feature; and
    an exterior bone-ingrowth portion having a proximal boundary extending adjacently parallel along the superior surface and extending distally over a portion of the stem, the proximal boundary extending distally at an angle to define an angled proximal boundary to cover the base of the neck, the first length of the lateral extent defined from the angled proximal boundary of the exterior bone-ingrowth portion to the center point of the head connecting feature;
    wherein the first length of the lateral extent ranges from 20% to about 50% of the lateral offset distance.

12. The prosthesis of claim 11, wherein the first length of the lateral extent ranges from 20% to 40% of the lateral offset distance.

13. The prosthesis of claim 11, wherein the first length of the lateral extent ranges from 20% to 30% of the lateral offset distance.

14. The prosthesis of claim 11, wherein the angled proximal boundary of the exterior bone-ingrowth portion is configured to correspond and align with the resected proximal end of the femoral bone.

15. The prosthesis of claim 11, wherein the exterior bone-ingrowth portion is a coating configured to enhance bone ingrowth.

16. The prosthesis of claim 11, wherein the exterior bone-ingrowth portion is porous.

17. The prosthesis of claim 11, wherein the superior surface comprises a rounded surface.

18. The prosthesis of claim 11, further comprising a prosthetic head configured to be coupled to the head connecting feature.

* * * * *